(12) United States Patent
Scarr et al.

(10) Patent No.: US 9,169,256 B2
(45) Date of Patent: Oct. 27, 2015

(54) ARTIFICIAL NUCLEIC ACIDS

(71) Applicant: Elitech Holding B.V., Spankeren (NL)

(72) Inventors: Noah Scarr, Seattle, WA (US); Eugeny A. Lukhtanov, Bothell, WA (US)

(73) Assignee: ELITechGroup B.V., Spankeren (NL)

( * ) Notice: Subject to any disclaimer, the term of this patent is extended or adjusted under 35 U.S.C. 154(b) by 57 days.

(21) Appl. No.: 14/208,530

(22) Filed: Mar. 13, 2014

(65) Prior Publication Data

US 2014/0275508 A1 Sep. 18, 2014

Related U.S. Application Data

(60) Provisional application No. 61/778,961, filed on Mar. 13, 2013.

(51) Int. Cl.
| | |
|---|---|
| *C07H 19/02* | (2006.01) |
| *C07H 19/04* | (2006.01) |
| *C07D 473/18* | (2006.01) |
| *C07D 473/34* | (2006.01) |
| *C07D 239/47* | (2006.01) |
| *C07D 239/54* | (2006.01) |
| *C07F 9/6561* | (2006.01) |
| *C07F 9/6512* | (2006.01) |
| *C07H 21/00* | (2006.01) |
| *C07F 7/18* | (2006.01) |

(52) U.S. Cl.
CPC ............ *C07D 473/18* (2013.01); *C07D 239/47* (2013.01); *C07D 239/54* (2013.01); *C07D 473/34* (2013.01); *C07F 7/1856* (2013.01); *C07F 9/65121* (2013.01); *C07F 9/65616* (2013.01); *C07H 21/00* (2013.01)

(58) Field of Classification Search
None
See application file for complete search history.

(56) References Cited

PUBLICATIONS

European Patent Office, International Search Report and Written Opinion, PCT Application No. PCT/US2014/025766, Feb. 11, 2015.
European Patent Office, Invitation to Pay Additional Fees, PCT Application No. PCT/US2014/025766, Nov. 10, 2014.
Ludek, O.R., et al; Divergent Synthesis and Biological Evaluation of Carbocyclic a-, iso- and 3'-epi-Nucleosides and their Lipophilic Nucleotide Prodrugs; Synthesis, vol. 2006, No. 8, Apr. 1, 2006.
Singha, K., et al; Synthesis of Isoaristeromycin from D-glucose, Indian Journal of Chemistry, vol. 10B, Oct. 1, 2001.
Roy, A., et al; Synthesis of (1R, 2R, 4S, 5R)-2,4-Dihydroxy-5-hydroxymethylcyclopentylamine and its Conversion to an Analogue of Aristeromycin, Synlett, vol. 1997, No. 11, Nov. 1, 1997.

*Primary Examiner* — Patrick Lewis
(74) *Attorney, Agent, or Firm* — Jackson Walker L.L.P.

(57) ABSTRACT

Artificial nucleosides including 2-methyl-nucleobase-substituted butane-1,3-diol nucleosides are disclosed. Four different stereoisomers of such nucleosides are possible. Oligonucleotides made up of the artificial nucleosides form homoduplexes of greater stability than DNA duplexes and have a reduced ability to hybridize to DNA or RNA.

5 Claims, 11 Drawing Sheets

(R,R)  (S,S)

(R,S)  (S,R)

| Seq# | Sequence (5'-3') | Seq# | Sequence (5'-3') | %AT |
|---|---|---|---|---|
| 1 | TACAAGATTTAT-H | 5 (complement to 1) | ATAAATCTTGTA-H | 83.33 |
| 2 | TACAAGATTTAC-H | 6 (complement to 2) | GTAAATCTTGTA-H | 75 |
| 3 | TTCAAGATGTAC-H | 7 (complement to 3) | GTACATCTTGAA-H | 66.67 |
| 4 | TCCACCGTCGAG-H | 8 (complement to 4) | CTCGACGGTGGA-H | 33.33 |

H – is a hexanol linker

ARTIFICIAL NUCLEIC ACIDS

This application claims priority to U.S. Provisional Patent Application Ser. No. 61/778,961, filed Mar. 13, 2013, entitled "Artificial Nucleic Acids," the entire contents of which are hereby incorporated by reference.

BACKGROUND

This disclosure pertains to artificial nucleic acids and, more particularly, to artificial nucleic acid backbones which do not hybridize well to DNA or RNA, as well as their production and uses, including for diagnostic and chemotherapeutic purposes.

For about the last 20 years, a number of nucleic acid analogues have been synthesized to modify or improve nucleic acid hybridization characteristics. The properties of the nucleic acid analogues can be classified as those which hybridize to natural nucleic acids and those that hybridize only to themselves and not to natural nucleic acids. Peptide nucleic acids exhibit strong hybridization with DNA and RNA (Nielsen et al, Science 254: 1497-1500 (1991) and similarly locked nucleic acids show increased stability and discrimination properties when hybridized to nucleic acids (Koshkin et al, *Tetrahedron* 54: 3607-3630 (1998)). Other nucleic acid analogues with DNA and RNA binding properties include pyrrolidinyl peptide nucleic acid (Vilaivan et al, Artificial DNA; PNA & XNA, 2: 50-59 (2011)).

Pyranosyl nucleic acid (p-RNA), and 3-deoxypyranosyl nucleic acid (p-DNA) are polymers that preferentially pair with complementary pRNA or pDNA versus natural DNA and RNA sequences (Schlonvogt et al. Helv. Chim. Acta 79, 2316 (1996), Ashkerman et al. *Helv. Chim., Acta* 85, 1443-1462 (2002)). Pentopyranosyl nucleic acid preparation and use for the production of a therapeutic, diagnostic and/or electronic component has been described (U.S. Pat. No. 6,506,896, U.S. Pat. No. 7,153,955).

Acyclic phosphodiester nucleic acid backbones have been disclosed, for example, for GNA (Zang et al.), aTNA (Asanuma et al., J. Am Chem Soc., 132: 14702-14703 (2010) and UNA (Peterson et al., Organic & Biomolecular Chemistry, 9(10):3591-3597 (2011). The (R)- and (S)-enantiomers of glycol nucleic acid (GNA) do not cross-pair with each other or with DNA: however. (S)-GNA cross-pairs with RNA (Johnson et al., J. Org. Chem., 76:7964-74 (2011): Zhang et al., J. Amer. Chem. Soc, 127: 4174-4175 (2005)). Benzene-phosphate backbone (Ueno et al., Nucl. Acids Symposium Series., 51: 293-294 (2007)) is another preferably self-hybridizing backbone. A number of purine and pyrimidine acyclic nucleosides were disclosed and tested as antivirals (Guillarme et al., Tetrahedron, 59: 2177-2184(2003)).

Depurination is the cleavage of the glycosidic bond connecting the purine base to sugar during oligonucleotides synthesis and during the synthesis of the purine phosphoramidites. Limitation of depurination requires special protecting groups and reaction conditions (Froehler and Matteucci. Nucl. Acids Res., 11: 8031-8036 (1983). McBride et al., J. Amer. Chem. Soc., 108: 2040-2048 (1986)). For these reasons, it is therefore desirable to utilize artificial nucleic acids that lack the glycosidic bond.

The design of multiple nucleic acid sequences with the same $T_m$ poses special challenges for use in applications such as microarrays and nano-fabrications. It is essential to prevent undesired hybridizations. It is also required that multiple nucleic acid sequences need to be designed that do not hybridize non-specifically with each other (Tanaka et al., Nucl. Acids. Res., 33: 903-911(2005)). These so-called orthogonal nucleic acids can be designed as described in U.S. Application Publication No. 2012/0015358. The orthogonal nucleic acids with low affinity for DNA or/and not recognizable by DNA processing enzymes can be especially useful for labeling, barcoding or anchoring of multiple DNA-containing substrates co-existing in one mixture or on one array.

SUMMARY

The present disclosure relates to artificial nucleosides, or nucleoside analogues, and nucleotides and oligonucleotides formed from these artificial nucleoside monomer units, and to oligonucleotides formed from artificial nucleoside monomer units in which one or more of the units is functionalized, and to the use of these novel compositions for diagnostic and chemotherapeutic purposes.

The preferred artificial nucleosides can be characterized as 2-((nucleobase)methyl)butane-1,3-diols. Four different stereoisomers of the nucleoside analogues are possible. The nucleoside analogues can form oligomers that can include one or more phosphodiester bonds. Oligomers made up of the nucleoside analogues can also be utilized to form conjugates with oligomers having a natural nucleic acid backbone, different non-natural backbones, peptides, and the like.

DETAILED DESCRIPTION OF PREFERRED EMBODIMENTS

I. General

The nucleoside analogues of the present disclosure can be generally represented by the following Formulas I and II:

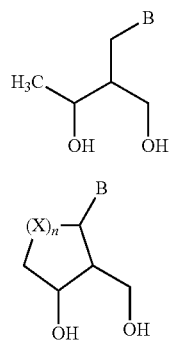

wherein B is a nucleic acid base which may be natural or artificial, X is —CH$_2$— or substituted carbon, and n is 1 or 2.

Preferred nucleoside analogues can be represented by the formulas shown below:

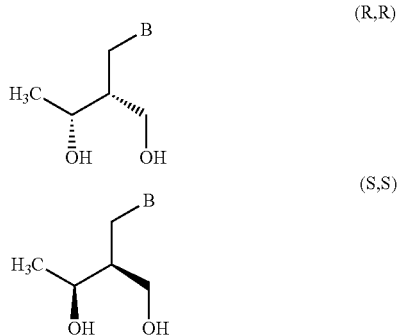

wherein B is a nucleic acid base which may be natural or artificial.

The preferred R,R stereoisomer of the nucleosides, when incorporated into oligonucleotides, forms homoduplexes of greater stability than DNA oligonucleotides of the same sequences. Oligonucleotides made up of the preferred R,R stereoisomer nucleosides demonstrate a reduced ability to hybridize to DNA to form heteroduplexes. Oligonucleotides made up of the preferred S,S stereoisomer nucleosides, the mirror image of the R,R steroisomers, demonstrate no ability to hybridize to DNA to form heteroduplexes because their orientation within the nucleic acid backbone is "left-handed" compared to a natural nucleic acid backbone. Furthermore, oligomers synthesized with the S,S steroisomers have the same self-hybridizing properties as the mirror image oligomers containing the R,R backbone.

Figure 1:
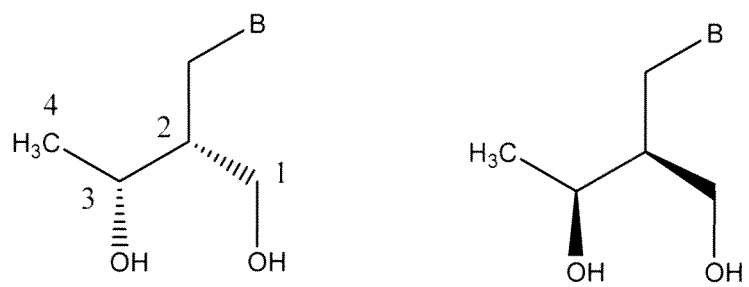
FIG. 1 shows four possible stereoisomers of 2-((nucleobase) methyl)butane-1,3-diols.
Figure 1:
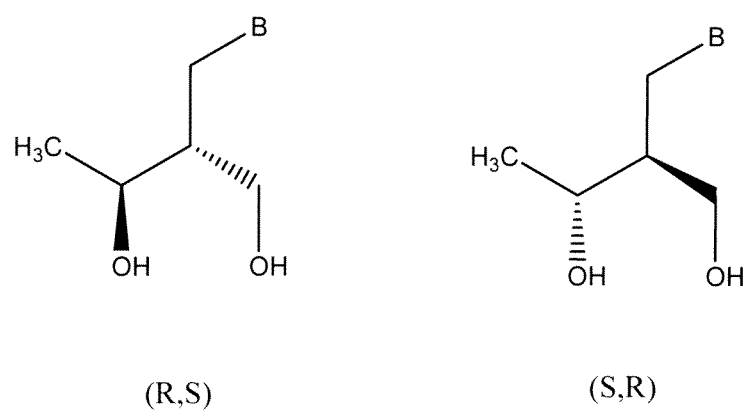

II. General Synthesis 2-((Nucleobase)methyl)butane-1,3-diols were generally prepared by Mitsunobu condensation of properly protected stereochemically pure 2-(hydroxymethyl)butane-1,3-diols with nucleobases or base precursors. Four different stereoisomers of such nucleosides are possible (FIG. 1).

Figure 2:
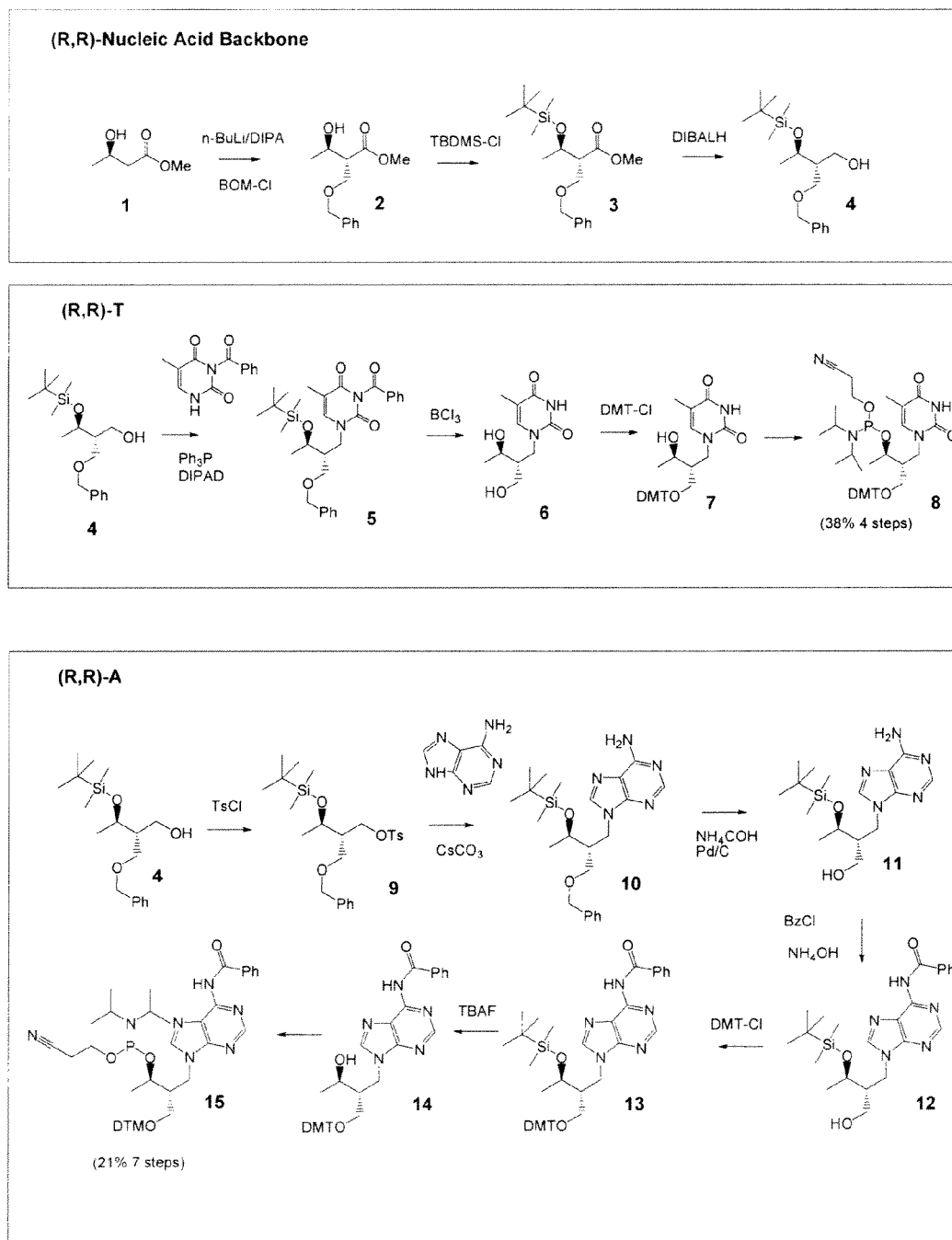
FIG. 2 shows a synthetic scheme for the preparation of (2R,3R)-2-((3,4-dihydro-5-methyl-2,4-dioxopyrimidin-1 (2H)-yl)methyl)butane-1,3-diol and (2R,3R)-2-((6-amino-9H-purin-9-yl)methyl)butane-1,3-diol and their respective phosphoramidites.
Figure 3:
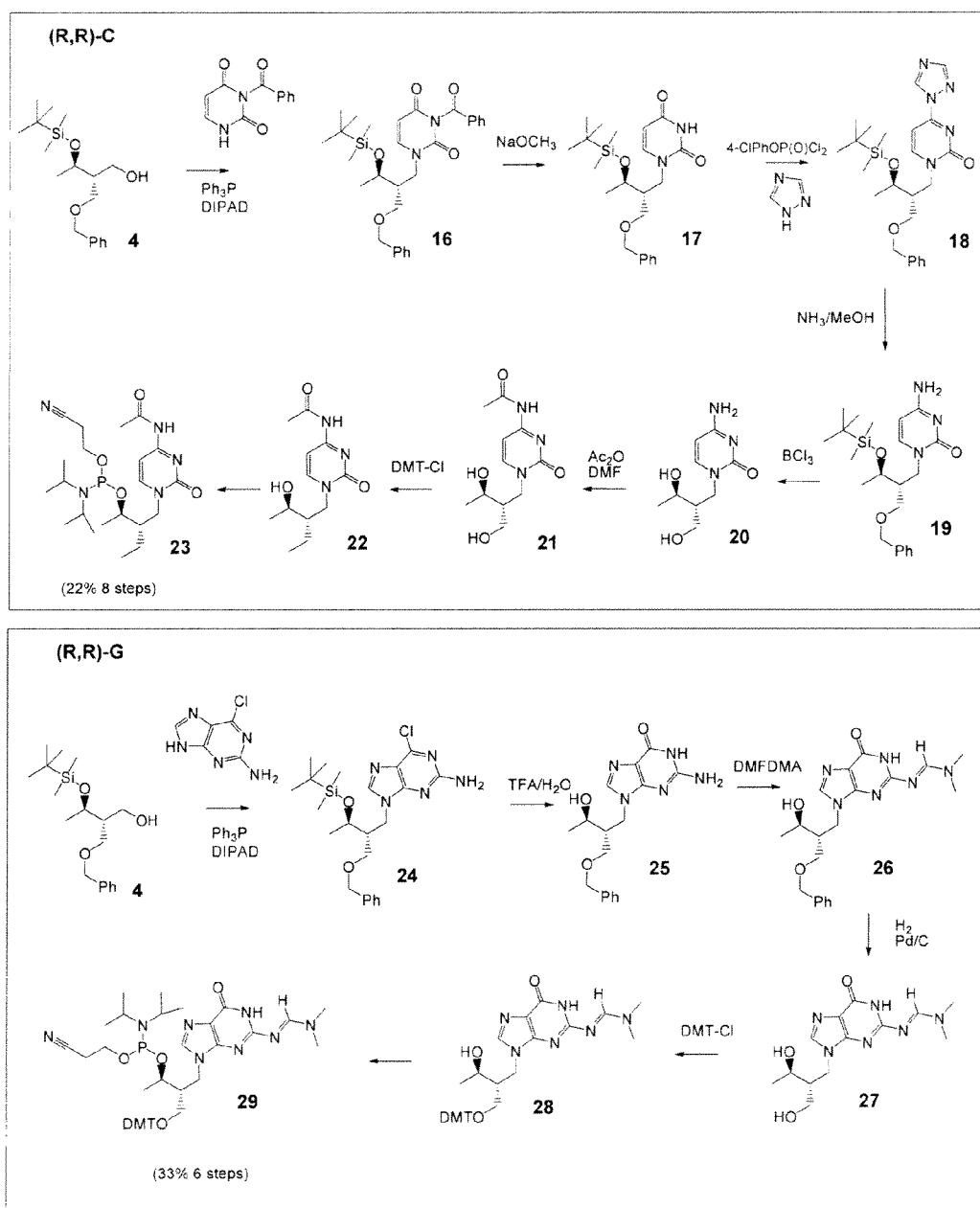
FIG. 3 shows a synthetic scheme for the preparation of (2R,3R)-2-((4-amino-2-oxopyrimidin-1(2H)-yl)methyl)butane-1,3-diol and (2R,3R)-2-((2-amino-1,6-dihydro-6-oxopurin-9-yl)methyl)butane-1,3-diol and their respective phosphoramidites.

The (R,R)-nucleosides were prepared starting from known (2R,3R)-2-((benzyloxy)methyl)-3-(tert-butyldimethylsiloxy)butan-1-ol (4, FIG. 2) (W. H. Ham et al. J. Org. Chem. 2000, 65, 8372-8374). The alcohol was condensed with thymine in the presence of triphenylphosphine and diisopropylazodicarboxylate to give protected nucleoside 5, which was then fully deprotected by a BCl$_3$ treatment to yield thymidine 6. DMT-protection of the primary hydroxyl followed with phosphitylation of the secondary hydroxyl group afforded thymidine phosphoramidite 8. To make the respective adenine analogue (FIG. 2), the alcohol 4 was, first, tosylated, and the resulting tosylate 9 was reacted with cesium salt of adenine generating protected adenosine 10. Hydrogenation to remove the benzyl protection followed by benzoylation of the exocyclic gave intermediate 12. DMT protection of the primary hydroxyl group and deprotection of the secondary hydroxyl with tetrabutylammonium fluoride yielded DMT-protected N-benzoyl adenosine 14. Standard phosphitylation of the secondary hydroxyl afforded 2-cyanoethyl diisopropylphosphoramidite 15 completing the synthesis in 21% overall yield starting from 4. To make a cytosine analogue with the same nucleic acid backbone structure, the alcohol 4 was, first, converted to protected uracil 16 (FIG. 3). Debenzoylation to 17 followed by activation of the 4 position of uracil via the formation of the triazo intermediate 18 and reaction with ammonia gave protected cytidine 19. The protecting groups of 19 were removed by a treatment with BCl$_3$ to give fully deprotected cytidine 20. The exocyclic amino-group of 20 was selectively acetylated to yield N-acetylcytidine 21, which was then protected by the DMT group and phosphitylated to afford cytidine phosphoramidite 23. The guanosine phosphoramidite 29 was prepared from the alcohol 4 in 6 steps in 33% overall yield (FIG. 3). The Mitsunobu condensation of 4 with 2-amino-6-chloropurine gave 2-amino-6-chloropurine nucleoside intermediate 24. Treatment with aqueous TFA replaced the chloro group with a hydroxyl group simultaneously removing the TBDMS protection. The resulting guanosine analogue 25 was protected at the exocyclic amine with a DMF group and hydrogenated to remove the benzyl protection freeing the primary hydroxyl. Standard DMT protection of 27 and phosphitylation of 28 completed the synthesis of guanosine phosphoramidite 29.

Figure 4:
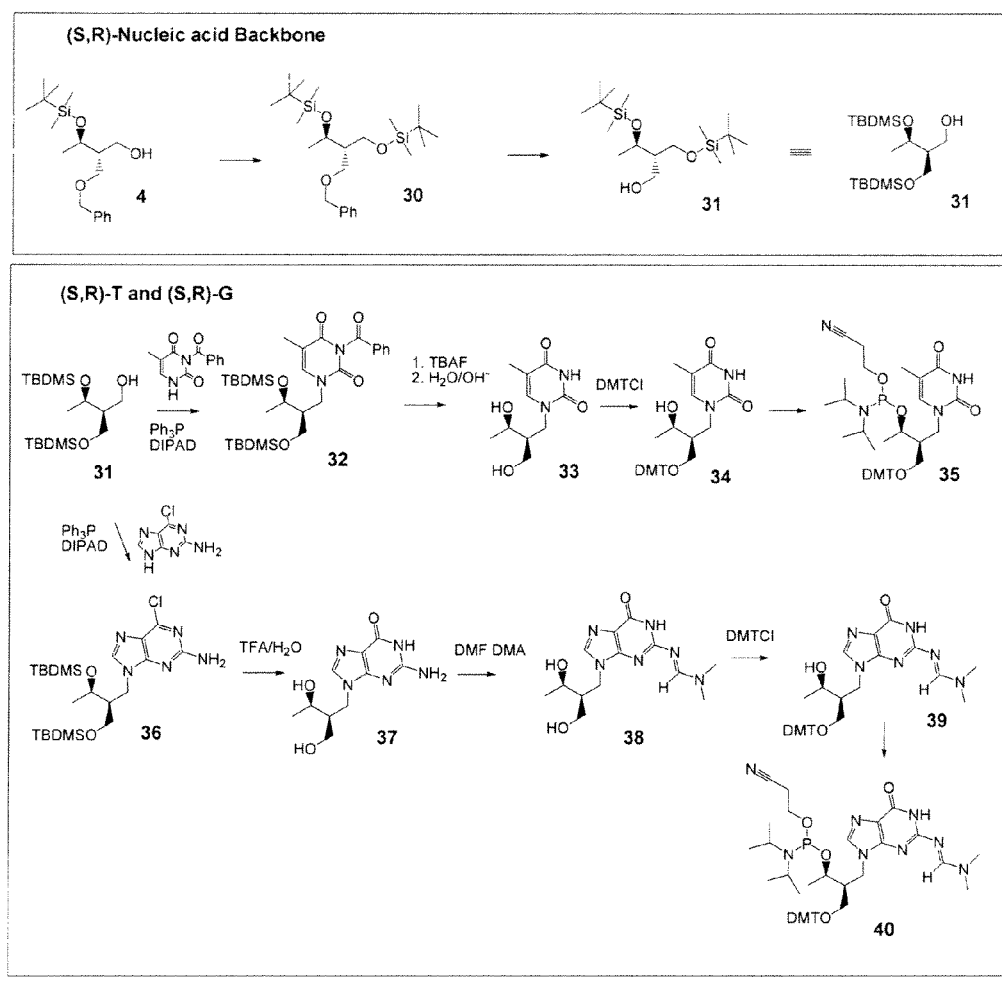
FIG. 4 shows a synthetic scheme for the preparation of (2S,3R)-2-((3,4-dihydro-5-methyl-2,4-dioxopyrimidin-1 (2H)-yl)methyl)butane-1,3-diol and (2S,3R)-2-((2-amino-1, 6-dihydro-6-oxopurin-9-yl)methyl)butane-1,3-diol and their respective phosphoramidites.
Figure 5:
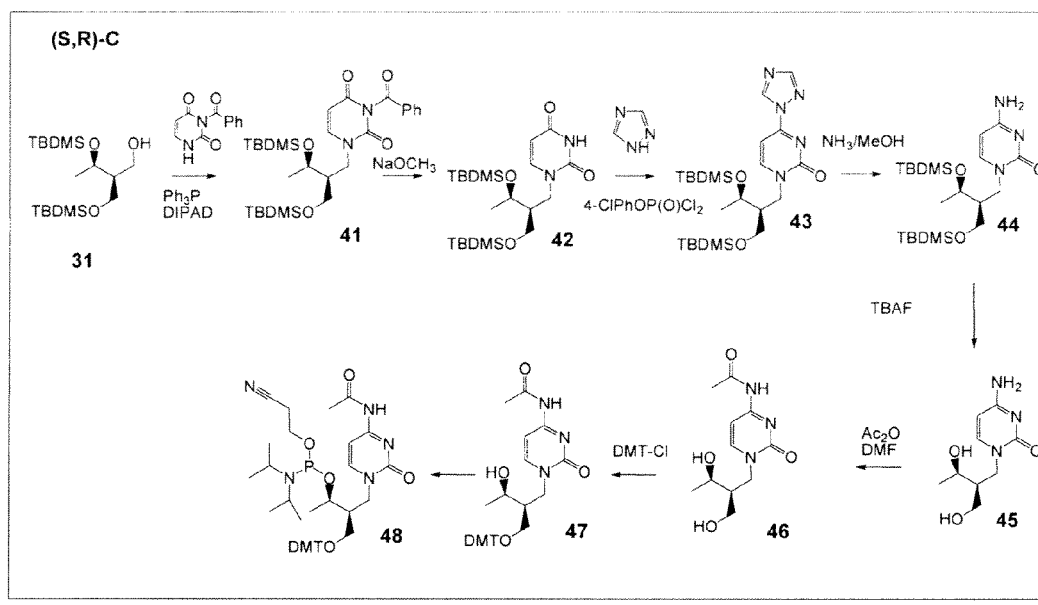
FIG. 5 shows a synthetic scheme for the preparation of (2S,3R)-2-((4-amino-2-oxopyrimidin-1(2H)-yl)methyl)butane-1,3-diol and (2S,3R,)-2(7-(adenyl)methy)butane-1,3-diol and their respective phosphoramidites.
Figure 5:
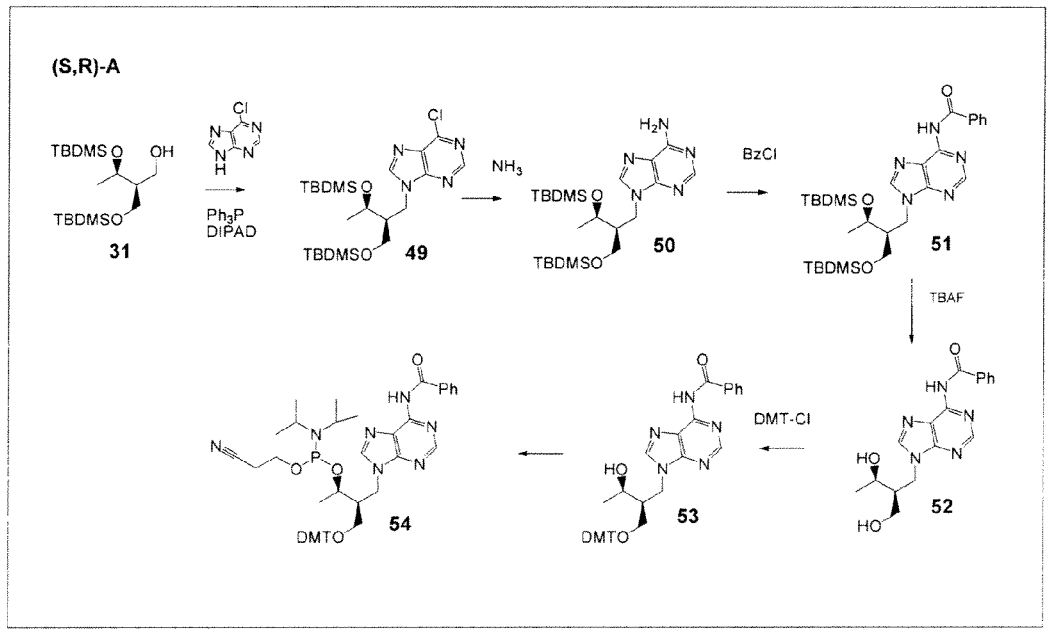

The starting alcohol 4 was also used to produce the (S,R) versions of 2-((nucleobase)methyl)butane-1,3-diols. It was sequentially protected with a TBDMS group and debenzylated to afford alcohol 31, starting material for the (S,R) nucleosides. The thymidine nucleoside 32 was obtained by Mitsunobu condensation of 31 with N-benzoylthymine. A treatment with TBAF removed both the TBDMS and benzoyl groups releasing the fully deprotected thymidine 33. DMT protection of the primary and phosphitylation of the secondary hydroxyls afforded 2-cyanoethyl phosphoramidite 35. The respective guanosine nucleoside phosphoramidite 40 (FIG. 4) was prepared similarly to its (R,R) analogue except that it did not require the hydrogenation step for debenzylation. So was the case with the cytidine analogue 48. The adenosine phosphoramidite 54 was synthesized in 7 steps. This time the initial condensation step was done using the Mitsunobu conditions, as oppose to alkylation using an activated tosylate in case of the (R,R) isomer (FIG. 2), using alcohol 31 and 6-chloropurine. The resulting chloropurine nucleoside 49 was aminated with ammonia (compound 50), benzoylated at the resulting exocyclic amine (compound 51) and reacted with TBAF to deblock the hydroxyl groups and yield N-benzoyl adenosine 52. Dimethoxytritylation (53) and the subsequent phosphitylation afforded the desired phosphoramidite 54.

Figure 7:
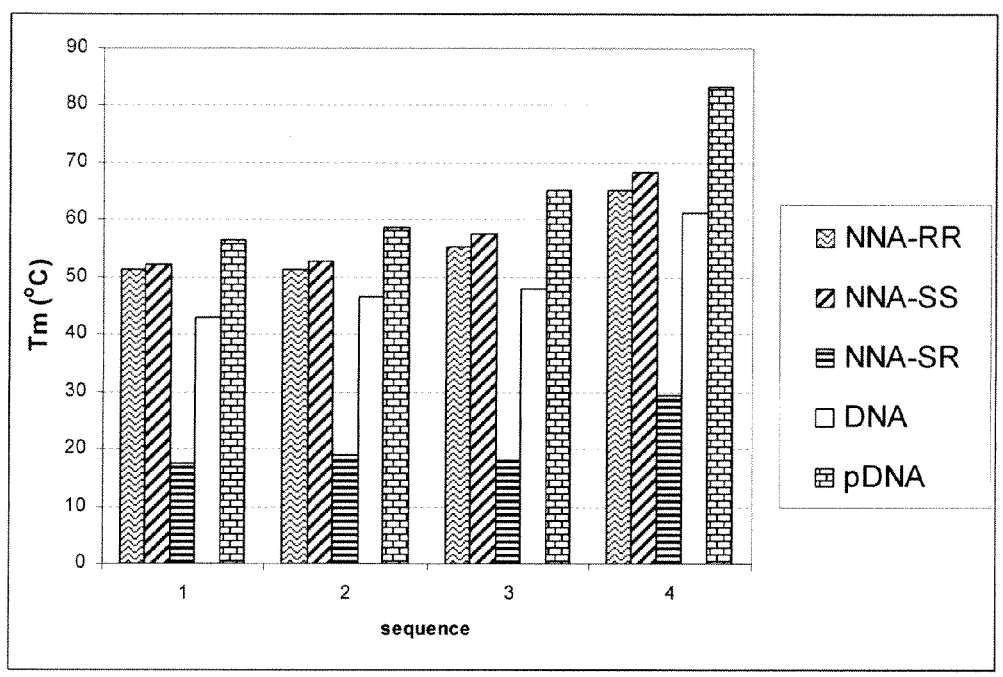
FIG. 7 shows a summary of melting temperatures for homoduplexes with various nucleic acid backbones and A/T composition.
Figure 8:
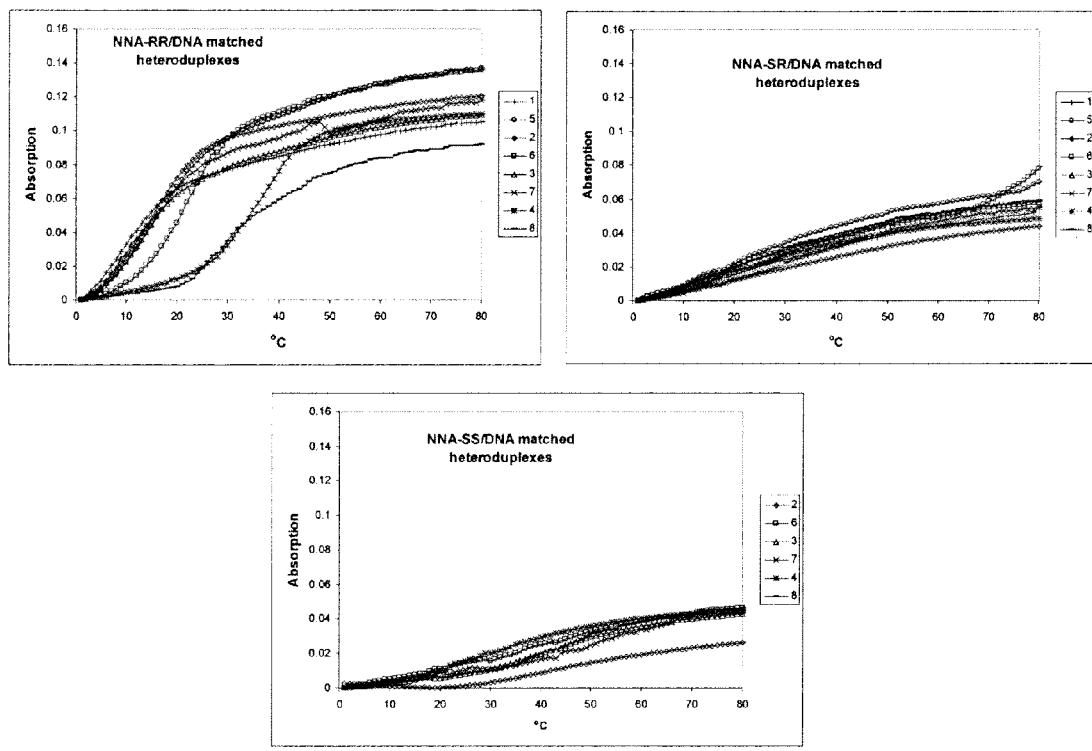
FIG. 8 shows melting curves for matched heteroduplexes with (2R,3R)-, (2S,3R)- and (2S,3S) 2-methylbutane-1,3-diol (NNA-RR, NNA-SR and NNA-SS) and DNA backbones and variable A/T composition.

A combination of the methods utilized to synthesize the (R,R) and (R,S) nucleosides was also used to synthesize the respective (S,S) stereoisomers of A, T, C and G nucleosides of general structure I starting from the (2S,3S) stereoisomer of compound 4. It has been shown that the (S,S) version of this nucleic acid backbone provides oligomers that form stable duplexes with complementary sequences of the same backbone (FIG. 7) but do not hybridize to natural DNA (FIG. 8). As expected, melting temperatures of the (S,S)-based and (R,R)-configured duplexes were essentially identical (FIG. 7).

Figure 10:
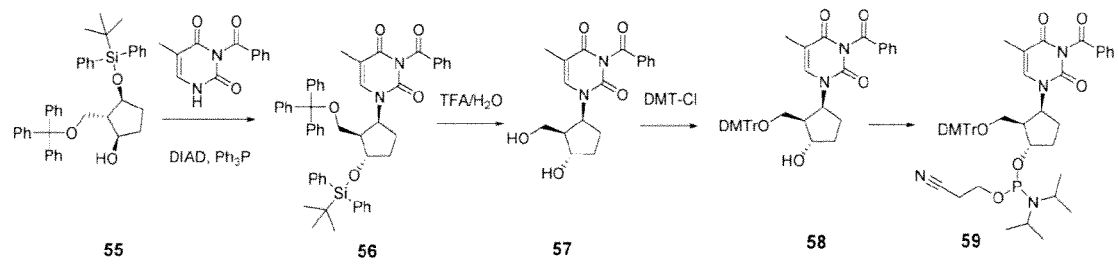
FIG. 10 shows a synthetic scheme for the preparation of a cyclopentane-based thymidine analogue and its respective phosphoramidite.
Figure 11:
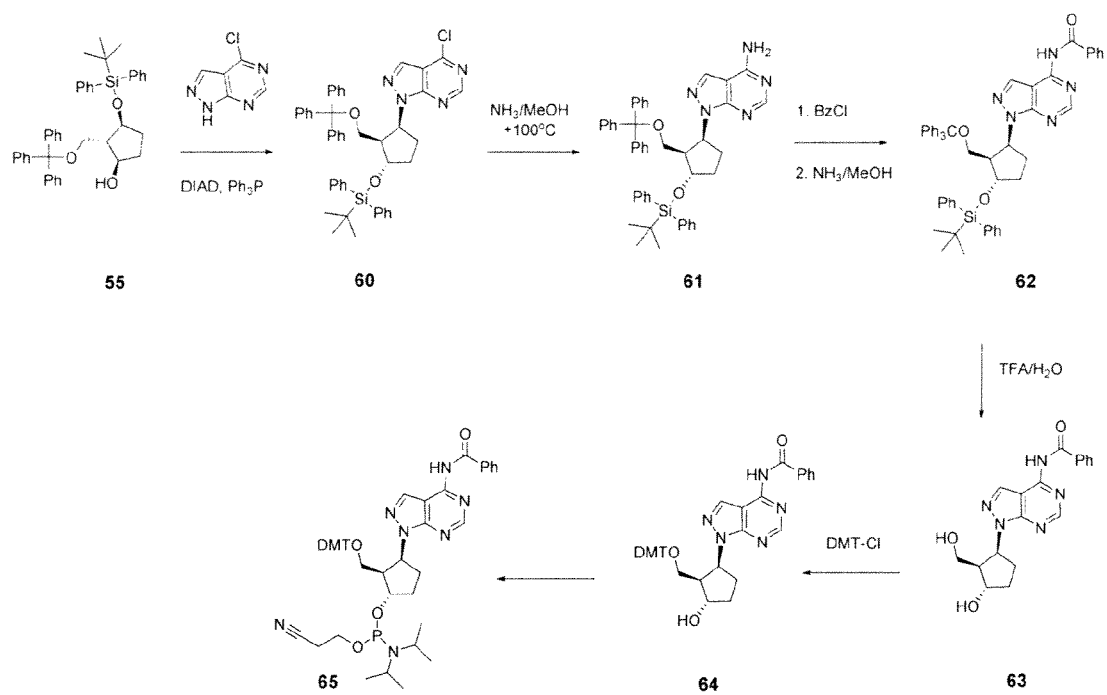
FIG. 11 shows a synthetic scheme for the preparation of a cyclopentane-based adenosine analogue and its respective phosphoramidite.

Cyclopentane-based nucleic acid monomers of the general structure II (X=—CH$_2$—, n=1) have also been synthesized. This structure can be viewed as a locked (with a —CH$_2$— bridging group) version of the nucleic acid backbone of structure I. The T and A nucleosides were prepared by Mitsunobu condensation of the suitably protected stereochemically pure (hydroxymethyl)cyclopentanediol 55, which had been prepared from penten-1-one as described in U.S. Patent Application Publication No. 2011/0251387, with a protected nucleobase (FIG. 10) or a base precursor (FIG. 11). The T monomer (compound 59) was further furnished by removing the transient trityl and silyl protections from the primary and secondary hydroxyls and installing respective DMT and phosphoramidite groups. Analogously, the A monomer after having been aminated and protected was converted to the DMT phosphoramidite of structure 65. The G and C monomers can be prepared by combination of the methods shown in FIGS. 3, 10 and 11.

The methods described in U.S. Patent Application Publication 2011/0251387, incorporated by reference, in combination with the known Mutsunobu-based stereo inversion of secondary hydroxyl group and the methods described herein provide synthetic routes to all 8 possible stereo configurations of nucleosides of Formula II (X=—CH$_2$—, n=1) above.

Cyclohexane-based nucleic acid monomers of the general structure II wherein X=—CH$_2$— and n=2 can be synthesized analogously using cyclohexen-1-one in place of cyclopenten-1-one as the starting material.

II. Definitions

Artificial bases include modified bases. Modified bases include naturally-occurring and synthetic modifications and analogues of the major bases such as, for example, hypoxanthine, 2-aminoadenine, 2-thiouracil, 2-thiothymine, inosine, 5-N$^4$-ethenocytosine, 4-aminopyrrazolo[3,4-d]pyrimidine and 6-amino-4-hydroxy-[3,4-d]pyrimidine. Any modified nucleotide or nucleotide analogue compatible with hybridization of probe with a target nucleic acid conjugate to a target sequence is useful, even if the modified nucleotide or nucleotide analogue itself does not participate in base-pairing, or has altered base-pairing properties compared to naturally-occurring nucleotides. Examples of modified bases are disclosed in U.S. Pat. Nos. 7,045,610; 5,824,796; 6,127,121; 5,912,340; and PCT Publications WO 01/38584; WO 01/64958, each of which is hereby incorporated herein by reference in its entirety. Preferred modified bases include 5-hydroxybutynyl uridine for uridine; 4-(4,6-Diamino-$^1$H-pyrazolo[3,4-d]pyrimidin-3-yl)-but-3-yn-1-ol, 4-amino-$^1$H-pyrazolo[3,4-d]pyrimidine, and 4-amino-$^1$H-pyrazolo[3,4-d] pyrimidine for adenine; 5-(4-Hydroxy-but-1-ynyl)-1H-pyrimidine-2,4-dione for thymine; and 6-amino-$^1$H-pyrazolo[3,4-d]pyrimidin-4(5H)-one for guanine. Particularly preferred modified bases are "Super A®: 4-(4,6-Diamino-1H-pyrazolo[3,4-d]pyrimidin-3-yl)-but-3-yn-1-ol," "Super G®: 4-hydroxy-6-amino pyrazolopyrimidine" (www.elitechgroup.com) and "Super T®: 5-(4-hydroxy-but-1-ynyl)-1H-pyrimidine-2,4-dione". 3-Alkynyl pyrazolopyrimidine analogues as universal bases are disclosed in U.S. Patent Application Publication No. 2012/0244535, incorporated by reference.

The terms "oligonucleotide," "nucleic acid," and "polynucleotide" are used interchangeably herein. These terms refer to a compound comprising nucleic acid, nucleotide, or its polymer in either single- or double-stranded form, e.g., DNA, RNA, analogues of natural nucleotides, and hybrids thereof. The terms encompass polymers containing modified or non-naturally-occurring nucleotides, or to any other type of polymer capable of stable base-pairing to DNA or RNA including, but not limited to, peptide nucleic acids as described in Nielsen et al., Science, 254:1497-1500 (1991), bicyclo DNA oligomers as described in Bolli et al., Nucleic Acids Res., 24:4660-4667 (1996), and related structures. Unless otherwise limited, the terms encompass known analogues of natural nucleotides that hybridize to nucleic acids in a manner similar to naturally-occurring nucleotides. Examples of such analogues include, without limitation, phosphorothioates, phosphoramidates, methyl phosphonates, chiral-methyl phosphonates, 2-O-methyl ribonucleotides, and peptide-nucleic acids (PNAs). A "subsequence" or "segment" refers to a sequence of nucleotides that comprise a part of a longer sequence of nucleotides.

The practice of the methods described herein will employ, unless otherwise indicated, conventional techniques in organic chemistry, biochemistry. oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example. Sambrook, Fritsch & Maniatis. MOLECULAR CLONING: A LABORATORY MANUAL, Second Edition, Cold Spring Harbor Laboratory Press (1989): Ausubel, et al., CURRENT PROTOCOLS IN MOLECULAR BIOLOGY. John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

EXAMPLES

The following examples are provided to illustrate, but not to limit, the subject matter described herein.

Example 1

(2R,3R)-1-Benzyloxy-3-(tert-butyldimethylsiloxy)-2-((3-benzoyl-3,4-dihydro-5-methyl-2,4-dioxopyrimidin-1(2H)-yl)methyl)butane (5)

To a cold (ice/water bath) solution of (2R,3R)-2-((benzyloxy)methyl)-3-(tert-butyldimethylsiloxy)butan-1-ol (4) (W.-H. Ham et al. J. Org. Chem. 2000, 65, 8372-8374) 1.5 g, 4.6 mmol), 3-benzoylthymine (1.5 g, 6.5 mmol) and triphenylphosphine (1.71 g, 6.5 mmol) in 50 ml of anhydrous THF was added dropwise via syringe with stirring (1.26 ml, 6.5 mmol) of diisopropylazodicarboxylate. The reaction was removed from the bath and stirred at room temperature for 2 hrs and then concentrated. The reaction was diluted with ether (50 ml) and hexane (50 ml) to precipitate some of triphenylphosphine oxide and the DIPADC by-product. The solids were filtered off and the filtrate concentrated. The resultant crude product, which still contained some $Ph_3PO$, was chromatographed on silica eluting with 20% ethyl acetate in hexane. Concentration of the pure product fractions afforded 2.0 g (81%) of 5 as a colorless viscous srup. $^1H$ NMR ($CDCl_3$): δ 7.85 (d, J=8.4 Hz, 2H), 7.58 (t, J=7.5 Hz, 1H), 7.42 (t, J=7.8 Hz, 2H), 7.35-7.25 (m, 5H), 7.06 (d, J=1.2 Hz, 1H), 4.42 (s, 2H), 3.98 (m, 2H), 3.61 (m, 1H), 3.46 (d, J=5.7 Hz, 2H), 2.08 (m, 1H), 1.83 (s, 3H), 1.16 (d, J=6.6 Hz, 3H), 0.84 (s, 9H), 0.02 (s, 3H), 0.00 (s, 3H).

Example 2

(2R,3R)-2-((3,4-Dihydro-5-methyl-2,4-dioxopyrimidin-1(2H)-yl)methyl)butane-1,3-diol (6)

To a cold (−77° C., acetone/dry ice bath) solution of 5 (2.0 g, 3.72 mmol) in 100 ml of anhydrous dichloromethane was added (via syringe) 38 ml of 1M $BCl_3$ in dichloromethane over 5 min. The reaction was stirred for 6 hrs until no more changes were observed by HPLC analysis and then quenched by adding a mixture of pyridine (26 ml) and methanol (54 ml) over 5 min. The reaction mixture was allowed to warm up to room temperature and concentrated. The resultant material was re-dissolved in methanol (100 ml) and co-evaporated twice with triethylamine (10 ml) to remove pyridine. The residue was suspended in dichloromethane and filtered to remove some triethylammonium chloride. The solid were washed with dichloromethane and the combined filtrates were concentrated and then chromatographed on silica eluting with 10% methanol in dichloromethane. Concentration of the pure product fractions afforded 0.6 g (70%) of nucleoside 6. $^1H$ NMR (DMSO-d6): δ 11.19 (s, 1H), 7.46 (s, 1H), 4.56 (d, J=4.8 Hz, 1H), 4.50 (t, J=5.1 Hz, 1H), 3.83 (m, 1H), 3.73 (m, 1H), 3.57 (m, 1H), 3.38 (m, 2H), 1.75 (s, 3H), 1.73 (m, 1H). 1.10 (d, J=6.3 Hz, 3H).

Example 3

(2R,3R)-1-Bis(4-methoxyphenyl)(phenyl)methoxy-3-((3,4-dihydro-5-methyl-2,4-dioxopyrimidin-1(2H)-yl)methyl)butan-3-ol (7)

To a stirred solution of 6 (0.6 g, 2.6 mmol) in 20 ml of anhydrous pyridine was added 1.05 g (3.1 mmol) of DMTCl. After being stirred at room temperature for 5 hrs the reaction was quenched with methanol (3 ml), concentrated and portioned between 10% citric acid and ethyl acetate. The organic phase was washed with saturated NaCl, dried over $Na_2SO_4$ and concentrated in vacuo to a solid foam. The crude product was chromatographed on silica eluting with ethyl acetate to afford 1.15 g (83%) of 7 as an amorphous white solid. $^1H$ NMR (DMSO-d6): δ 11.13 (s, 1H), 7.3 (m, 5H, 7.13 (m, 5H), 6.84 (m, 4H), 4.61 (d, 4.8 Hz, 1H), 3.75 (m, 2H), 3.73 (s, 6H), 3.65 (m, 1H), 3.10 (m, 1H), 2.88 (m, 1H), 2.00 (m, 1H), 1.66 (s, 3H), 1.01 (d, J=6.3 Hz, 3H).

Example 4

(2R,3R)-1-Bis(4-methoxyphenyl)(phenyl)methoxy-2-((3,4-dihydro-5-methyl-2,4-dioxopyrimidin-1(2H)-yl)methyl)butan-3-yl 2-cyanoethyl N,N-diisopropylphosphoramidite (8)

To a stirred solution of 7 (1.1 g, 2.07 mmol) in 30 ml of anhydrous dichloromethane was added diisopropylammonium tetrazolide (0.37 g) followed by 0.8 g (2.66 mmol) of 2-cyanoethyl N,N,N',N'-tetraisopropylphosphordiamidite. After being stirred at room temperature overnight the reaction n/us concentrated, and the residue portioned between ethyl acetate and saturated $NaHCO_3$. The organic phase was washed with saturated NaCl, dried over $Na_2SO_4$ and concentrated in vacuo. The crude phosphoramidite was precipitated twice by re-dissolving in small (~15 ml) amount of ethyl acetate, diluting with hexane (100 ml), allowing to settle as an oil and decanting the liquid. Drying in vacuo afforded 1.3 g (86%) of 8 as an amorphous white solid. $^{31}P$ NMR (DMSO-d6): δ 146.94, 145.89.

Example 5

(2R,3R)-2-((Benzyloxy)methyl)-3-(tert-butyldimethylsiloxy)butan-1-yl 4-methylbenzenesulfonate (9)

p-Toluenesulfonyl chloride (1.4 g. 7.4 mmol) was added in one portion to a cold (ice/water bath) stirred solution of 4 (2.0 g, 6.16 mmol) in anhydrous pyridine (25 ml). The reaction was allowed to warm up to room temperature and stirred for 6 hrs until no starting material was found by HPLC analysis. Ethyl acetate (100 ml) and 10% citric acid (enough to neutralize pyridine) were added. The organic phase was washed with saturated NaCl, saturated $NaHCO_3$ and dried over $MgSO_4$. The crude tosylate 9 (2.9 g) was used in the next step without additional purification. $^1H$ NMR ($CDCl_3$): δ 7.80 (d, J=8.1 Hz, 2H). 7.40-7.25 (m, 7H), 4.41 (d, J=3.6 Hz, 2H), 4.25 (m, 1H), 4.11 (m, 1H), 3.98 (m, 1H), 3.45 (m, 2H), 2.45 (s, 3H), 1.96 (m, 1H), 1.12 (d, J=6.3 Hz, 3H), 0.83 (s, 9H), 0.036 (s, 3H), 0.00 (s, 3H).

Example 6

(2R,3R)-1-Benzyloxy-3-(tert-butyldimethylsiloxy)-2-((6-amino-9H-purin-9-yl)methyl)butane (10)

To a suspension of adenine (1.22 g, 9.1 mmol) in 25 ml of anhydrous DMF was added 2.96 g of $Ce_2CO_3$ (hydrate) and the mixture was stirred at 100° C. for 15 min. A solution of 9 (2.9 g, ~7.4 mmol) in 20 ml of DMF was added in one portion. The reaction was stirred at 100° C. for 4 hrs until no starting material was found by HPLC, then cooled and filtered to remove unreacted adenine and cesium salts. The filtrate was concentrated, re-dissolved in ethyl acetate, washed with water, saturated NaCl and dried under $Na_2SO_4$. The crude product obtained after solvent evaporation was chromatographed on silica eluting with a gradient of acetone (20-35%) in ethyl acetate. Concentration of the pure product fractions and drying in vacuo afforded 1.2 g (37%) of 10 as a pale yellow viscous syrup. $^1H$ NMR ($CDCl_3$): δ 8.32 (s, 1H), 7.70 (s, 1H), 7.24 (m, 5H), 5.64 (s, 2H), 4.38 (m, 1H), 4.34 (d, 8.1 Hz, 2H), 4.16 (m, 1H), 4.02 (m, 1H), 3.32 (m, 2H), 2.23 (m, 1H), 1.14 (d, J=6.3 Hz, 3H), 0.85 (s, 9H), 0.015 (s, 3H), 0.00 (s, 3H).

Example 7

(2R,3R)-3-(tert-Butyl)(dimethyl)siloxy-2-((6-amino-9H-purin-9-yl)methyl)butan-1-ol (11)

To a solution of 10 (1.2 g, 2.7 mmol) in 80 ml of MeOH were added 10% Pd/C (0.5 g) and ammonium formate (3 g). The mixture was refluxed for 2 days until no starting material was found by HPLC analysis. The reaction was filtered through Celite and concentrated to give 11 as a white amorphous sold (0.9 g, 95%), which was sufficiently pure to be used in the next step without additional purification. $^1$H NMR (DMSO-d6): δ 8.12 (s, 1H), 8.07 (s, 1H), 7.17 (s, 2H), 4.61 (br s, 1H), 4.24 (m, 1H), 4.08 (m, 1H), 3.98 (m, 1H), 3.32 (m, 2H), 2.03 (m, 1H), 1.15 (d, J=6.6 Hz, 3H), 0.85 (s, 9H), 0.00 (s, 6H).

Example 8

(2R,3R)-3-(tert-Butyldimethylsiloxy)-2-((6-benzamido-9H-purin-9-yl)methyl)butan-1-ol (12)

Compound 11 (0.9 g, 2.56 mmol) was dried by co-evaporation with anhydrous pyridine (20 ml), then re-dissolved in a fresh portion of pyridine (20 ml) and cooled to about 0° C. (ice/water bath) and treated with 0.9 ml (7.3 mmol) of chlorotrimethylsilane. The reaction was stirred at 0° C. for 1 hr. Benzoyl chloride 1.5 ml (12.3 mmol) was added with stirring over 2 min. After having been warmed up to room temperature the reaction was left stirring for 2 hrs and then treated with water (5 ml) and conc. NH$_4$OH (10 ml). The deprotection was allowed to proceed for about 1 h until all bis-benzoyl intermediates were converted to the desired mono-benzoyl derivative 12. The reaction was concentrated, re-suspended in ethyl acetate, filtered to remove some partially precipitated benzamide, washed with 10% citric acid, saturated NaCl and dried over Na$_2$SO$_4$. Concentration of the filtrate resulted in crystallization of the desired product, which was collected by re-suspending the crystals in small amount of ethyl acetate/hexane (1:1) and filtration (0.69 g). The solid obtained from concentration of the filtrate was chromatographed on silica eluting with a gradient of acetone (0-20%) in ethyl acetate yielding 0.14 g of 12. Total yield—0.83 g (71%). $^1$H NMR (DMSO-d6): δ 11.08 (s, 1H), 8.70 (s, 1H), 8.42 (s, 1H), 8.00 (d. J=8.4 Hz, 2H), 7.61 (m, 1H), 7.51 (t, J=7.5 Hz, 2H), 4.58 (t, J=4.8 Hz, 1H), 4.37 (m, 1H), 4.17 (m, 1H), 4.00 (m, 1H), 3.32 (m, 2H), 2.08 (m, 1H), 1.18 (d, J=6.6 Hz, 3H), 0.84 (s, 9H), 0.00 (s, 6H).

Example 9

(2R,3R)-3-(tert-Butyldimethylsiloxy)-2-((6-benzamido-9H-purin-9-yl)methyl)-1-(bis(4-methoxyphenyl)(phenyl)methoxy)butane (13)

DMTCl (0.8 g. 2.37 mmol) was added in one portion to a stirred solution of 12 (0.82 g, 1.8 mmol) in 20 ml of anhydrous pyridine. The reaction was kept at room temperature for 20 hrs, concentrated and partitioned between ethyl acetate and 10% citric acid. The organic phase was washed with saturated NaCl, dried over Na2SO4 and concentrated. The resultant crude product was chromatographed on silica eluting with 50% ethyl acetate in hexane. Concentration of the pure product fractions afforded 1.2 g (88%) of 13 as a white amorphous solid. $^1$H NMR (DMSO-d6): δ 11.12 (s, 1H), 8.70 (s, 1H), 8.38 (s, 1H), 8.05 (d, J=8.7 Hz, 2H), 7.65 (m, 1H), 7.55 (t, J=7.5 Hz. 2H), 7.18 (m, 5H), 7.04 (t, J=8.7, 4H), 6.77 (m, 4H), 4.36 (m, 1H), 4.24 (m, 1H), 4.02 (m, 1H), 3.60 (s, 6H), 3.12 (m, 1H), 2.95 (m, 1H), 2.39 (m, 1H), 1.14 (d, J=6.6 Hz, 3H), 0.74 (s, 9H), 0.00 (s, 3H), −0.10 (s, 3H).

Example 10

(2R,3R)-2-((6-Benzamido-9H-purin-9-yl)methyl)-1-(bis(4-methoxyphenyl)(phenyl)methoxy)butan-3-ol (14)

A solution of tetrabutylammonium fluoride 1M in THF (3 ml) was added to a solution of 13 (1.1 g, 1.45 mmol) in 10 ml of THF. The reaction was kept at room temperature for 2 days until no staring material was seen by HPLC analysis. The reaction was concentrated and partitioned between water and ethyl acetate. The organic phase was washed with saturated NaCl, dried over Na$_2$SO$_4$ and concentrated. The resulting material was chromatographed on silica eluting with a gradient of acetone (0-40%) in ethyl acetate. Concentration of the pure product fractions afforded 0.9 g (96%) of 14 as a white amorphous solid. $^1$H NMR (DMSO-d6): δ 11.12 (s, 1H), 8.70 (s, 1H), 8.34 (s, 1H), 8.05 (d, J=8.7 Hz, 2H), 7.65 (m, 1H), 7.56 (t, J=7.5 Hz, 2H), 7.18 (m, 5H), 7.04 (m, 4H), 6.77 (m, 4H), 4.79 (d, J=4.8 Hz, 1H), 4.39 (m, 2H), 3.80 (m, 1H), 3.71 (s, 6H), 3.09 (m, 1H), 2.88 (m, 1H), 2.31 (m, 1H), 1.03 (d, J=6.3 Hz, 3H).

Example 11

(2R,3R)-1-(Bis(4-methoxyphenyl)(phenyl)methoxy)-2-((6-benzamido-9H-purin-9-yl)methyl)butan-3-yl 2-cyanoethyl N,N-diisopropylphosphoramidite (15)

To a stirred solution of 14 (0.9 g, 1.4 mmol) in 20 ml of anhydrous dichloromethane was added diisopropylammonium tetrazolide (0.25 g) followed by 0.5 g (1.66 mmol) of 2-cyanoethyl N,N,N',N'-tetraisopropylphosphordiamidite. In about 5 hrs another 0.04 g of 2-cyanoethyl N,N,N',N'-tetraisopropylphosphordiamidite was added. The reaction was allowed to proceed for total 20 hrs and then concentrated. The resultant semi-solid was portioned between ethyl acetate and saturated NaHCO$_3$. The organic phase was washed with saturated NaCl, dried over Na$_2$SO$_4$ and concentrated in vacuo. The crude phosphoramidite was precipitated twice by re-dissolving in small (~5-10 ml) amount of ethyl acetate, diluting with hexane (100 ml), allowing to settle as an oil and decanting the liquid. Drying in vacuo afforded 1.1 g (93%) of 15 as a white amorphous solid. $^{31}$P NMR (DMSO-d6): δ 147.11, 146.16.

Example 12

(2R,3R)-1-Benzyloxy-3-(tert-butyldimethylsiloxy)-2-((3-benzoyl-3,4-dihydro-2,4-dioxopyrimidin-1(2H)-yl)methyl)butane (16)

To a cold (ice/water bath) solution of 4 (2.3 g. 7.09 mmol), 3-benzoyluracyl (2.1 g, 10 mmol) and triphenylphosphine (3.8 g, 14.5 mmol) in 75 ml of anhydrous THF was added dropwise via syringe with stirring (2.94 ml, 15 mmol) of diisopropylazodicarboxylate. The reaction was removed from the bath and stirred at room temperature for 2 hrs and then concentrated. The resulting mixture was chromatographed on silica eluting with a gradient of ethyl acetate (20-33%) in hexane. Concentration of the product-containing fractions afforded 4.5 g of crude 16 which was still contained about 2 eqv. of hydrazine N,N'-bis(isopropyl)carbamate, the DIPADC by-product. $^1$H NMR (DMSO-d6): δ 7.87 (d, J=8.4 Hz, 2H), 7.82 (d, J=8.1 Hz, 2H), 7.76 (t, J=8.3 Hz, 1H), 7.54 (t, J=8.1 Hz, 2H), 7.31 (m, 5H), 5.78 (d, J=8.1 Hz, 1H), 4.42 (d, J=4.8 Hz, 2H), 3.95 (m, 2H), 3.73 (m, 1H), 3.45 (d, J=5.7 Hz, 2H), 2.09 (m, 1H), 1.13 (d, J=5.7 Hz, 3H), 0.83 (s, 9H), 0.02 (s, 3H), 0.00 (s, 3H).

Example 13

(2R,3R)-1-Benzyloxy-3-(tert-butyldimethylsiloxy)-2-((3,4-dihydro-2,4-dioxopyrimidin-1(2H)-yl)methyl)butane (17)

To a solution of 16 (about 4.6 mmol) in 100 ml of MeOH as added 2 ml of 25% NaOCH$_3$ in MeOH. After being kept at room temperature for 15 hrs the reaction was quenched by adding 1.5 g of solid triethylammonium chloride and concentrated. The resulting material was partitioned between water and ethyl acetate. The organic phase was washed with saturated NaCl, dried over $Na_2SO_4$ and concentrated to an oil, which was then chromatographed on silica eluting with a gradient of ethyl acetate (33-50%) in hexane. Concentration of the pure product fractions afforded 1.7 g (about 88%) of 17 as a white crystalline solid. $^1$H NMR (DMSO-d6): δ 11.18 (s, 1H), 7.52 (d, J=7.8 Hz, 1H), 7.28 (m, 5H), 5.47 (d, J=7.8 Hz, 1H), 4.38 (s, 2H), 3.97 (m, 1H), 3.84 (m, 1H), 3.62 (m, 1H), 3.38 (m, 2H), 2.02 (m, 1H), 1.13 (d, J=5.7 Hz, 3H), 0.84 (s, 9H), 0.01 (s, 3H), 0.00 (s, 3H).

Example 14

(2R,3R)-1-Benzyloxy-3-(tert-butyldimethylsiloxy)-2-((2-oxo-4-(1H-1,2,4-triazol-1-yl)pyrimidin-1(2H)-yl)methyl)butane (18)

To a cold (ice/water bath) solution of 17 (1.7 g, 4.06 mmol) and 1,2,4-triazole (3.9 g, 56.4 mmol) in 25 ml of anhydrous pyridine was added dropwise over 5 min 2.8 g (11.4 mmol) of 4-chlorophenyldichlorophosphate (via syringe). The reaction was allowed to warm up and kept at room temperature for 3 days until all starting material and some intermediates converted to the desired triazolide 18 (monitored by HPLC). The reaction was concentrated and partitioned between ethyl acetate (150 ml) and water (150 ml). The organic phase was washed with 10% citric acid. saturated NaCl and dried over $Na_2SO_4$. The crude material obtained after concentration of the extract was chromatographed on silica eluting with a gradient of ethyl acetate (33-50%) in hexane. Concentration of the pure product fractions afforded 1.5 g (79%) of 18 as a light tan crystalline solid. $^1$H NMR (DMSO-d6): δ 9.34 (s, 1H), 8.35 (s, 1H), 8.34 (d, J=7.2 Hz, 1H), 7.17 (m, 5H), 6.79 (d, J=7.2 Hz), 4.30 (s, 2H), 4.10 (m, 1H), 4.00 (m, 1H), 3.82 (m, 1H), 3.42 (d, J=5.7 Hz, 2H), 2.19 (m, 1H), 1.14 (d, J=6.3 Hz, 3H), 0.83 (s, 9H), 0.01 (s, 3H), 0.00 (s, 3H).

Example 15

(2R,3R)-1-Benzyloxy-3-(tert-butyldimethylsiloxy)-2-((4-amino-2-oxo-pyrimidin-1(2H)-yl)methyl)butane (19)

A solution of 18 (1.5 g, 3.2 mmol) in 100 ml of 6 M $NH_3$/MeOH was heated at 100° C. in a Parr bomb for 2 days. The reaction was cooled, concentrated and chromatographed on silica eluting with 10% MeOH in ethyl acetate. Concentration of the product-containing fractions afforded 1.27 g (95%) of 19 as an off-white amorphous solid. $^1$H NMR (DMSO-d6): δ 7.43 (d, J=7.2 Hz, 1H), 7.29 (m, 5H), 6.97 (br s, 2H), 5.58 (d, J=7.2 Hz), 4.39 (d, J=1.8 Hz, 2H), 3.98 (m, 1H), 3.83 (m, 1H), 3.51 (m, 1H), 3.35 (m, 2H), 2.06 (m, 1H), 1.14 (d, J=6.3 Hz, 3H), 0.85 (s, 9H), 0.02 (s, 3H), 0.00 (s, 3H).

Example 16

(2R,3R)-2-((4-Amino-2-oxo-pyrimidin-1(2H)-yl)butane-1,3-diol (20)

To a cold (~−77° C., acetone/dry ice bath) solution of 19 (1.2 g, 2.87 mmol) in 50 ml of anhydrous dichloromethane was added via syringe 19 ml (19 mmol) of 1 M $BCl_3/CH_2Cl_2$. The reaction was stirred for 10 hrs and quenched with a mixture of methanol (27 ml) and pyridine (13 ml). The reaction was warmed up, concentrated, co-evapoarated with a triethylamine/MeOH mixture to remove pyridine and chromatographed on C18 (5×25 cm) column eluting with a gradient of acetonitrile (0-15%). Concentration of the pure product fractions afforded 0.5 g (82%) of nucleoside 20 as a white solid. $^1$H NMR (DMSO-d6): δ 7.52 (d, J=7.2 Hz, 1H), 7.01 (br s, 2H), 5.65 (d, J=7.2 Hz), 4.70 (d, J=4.8 Hz, 1H), 4.62 (t, J=5.4 Hz, 1H), 3.84 (m, 1H), 3.63 (m, 2H), 3.34 (m, 1H), 3.25 (m, 1H), 1.68 (m, 1H), 1.08 (d, J=6.3 Hz, 3H).

Example 17

(2R,3R)-2-((4-Acetamido-2-oxo-pyrimidin-1(2H)-yl)methyl)butane-1,3-diol (21)

To a solution of 20 (0.5 g, 2.34 mmol) in 12 ml of anhydrous DMF was added dropwise with stirring 0.243 ml (2.57 mmol) of acetic anhydride. The reaction was kept at room temperature for 3 days and then concentrated. The oily residue was dried by co-evaporation with xylene and then in vacuo to afford 0.65 g (108%) of 21 (contaminated with some DMF) as a white solid, which was sufficiently pure to be used in the next step without additional purification. $^1$H NMR (DMSO-d6): δ 10.81 (s, 1H), 8.00 (d, J=7.2 Hz, 1H), 7.13 (d, J=7.2 Hz, 1H), 4.62 (d, J=5.1 Hz, 1H), 4.53 (t, J=4.8 Hz, 1H), 4.02 (m, 1H), 3.73 (m, 2H), 3.53 (m, 2H), 2.09 (s, 3H), 1.80 (m, 1H), 1.10 (d, J=6.3 Hz, 3H).

Example 18

(2R,3R)-1-(Bis(4-methoxyphenyl)(phenyl)methoxy)-2-((4-acetamido-2-oxo-pyrimidin-1(2H)-yl)methyl)butan-3-ol (22)

DMTCl (0.9 g, 2.66 mmol) was added to a stirred solution of 21 (0.6 g, 2.35 mmol) in 25 ml of anhydrous pyridine. After being stirred at room temperature for 4 hrs the reaction was quenched with MeOH (2 ml) and concentrated to an oil. The oil was partition between dichloromethane and 10% citric acid. The organic phase was washed with saturated NaCl, dried over $Na_2SO_4$ and concentrated. The resulting material was chromatographed on silica eluting with a gradient of methanol (5-7.5%) in ethyl acetate. Concentration of the pure product fractions afforded 1.2 g (91%) of 22 as a white amorphous solid. $^1$H NMR (DMSO-d6): δ 10.78 (s, 1H), 7.77 (d, J=7.2 Hz, 1H), 7.27 (m, 5H), 6.97 (d, J=7.2 Hz, 1H), 6.84 (m, 4H), 4.66 (d, J=4.8 Hz, 1H), 4.01 (m, 1H), 3.78 (m, 2H), 3.73 (s, 6H), 3.73 (m, 1H), 3.09 (m, 2H), 2.89 (m, 1H), 2.12 (m, 1H), 2.09 (s, 3H), 1.02 (d, J=6.3 Hz, 3H).

Example 19

(2R,3R)-1-(Bis(4-methoxyphenyl)(phenyl)methoxy)-2-((4-acetamido-2-oxo-pyrimidin-1(2H)-yl)methyl)butan-3-yl 2-cyanoethyl N,N-diisopropylphosphoramidite (23)

To a stirred solution of 22 (1.0 g, 1.79 mmol) in 25 ml of anhydrous dichloromethane was added diisopropylammonium tetrazolide (0.35 g) followed by 0.8 g (2.66 mmol) of 2-cyanoethyl N,N,N',N'-tetraisopropylphosphordiamidite. After being stirred at room temperature for 20 hrs the reaction was concentrated, and the residue portioned between ethyl acetate and saturated $NaHCO_3$. The organic phase was washed with saturated NaCl, dried over $Na_2SO_4$ and concentrated in vacuo. The crude phosphoramidite was precipitated twice by re-dissolving in small (~10 ml) amount of ethyl acetate, diluting with hexane (100 ml), allowing precipitate as an oil and decanting the liquid. Drying in vacuo afforded 1.2 g (88%) of 23 as an amorphous white solid. $^{31}$P NMR (DMSO-d6): δ 148.03, 147.19.

Example 20

(2R,3R)-1-Benzyloxy-3-(tert-butyldimethylsiloxy)-2-((2-amino-6-chloro-9H-purin-9-yl)methyl)butane (24)

To a cold (~0° C., ice/water bath) mixture of 2-amino-6-chloropurine (2.2 g. 13.2 mmol), 4 (3.9 g, 12 mmol), triphenylphosphine (3.52 g, 13.4 mmol) in 50 ml of anhydrous THF was added with stirring 2.75 ml (13.9 mmol) of diisopropylazodicarboxylate. The reaction was stirred at room temperature for 5 hrs. The solvent was removed in vacuo and the residue chromatographed on silica eluting with a gradient of ethyl acetate (20-66%) in hexane. The product-containing fractions were pooled and concentrated to afford a semi-crystalline material, which was re-suspended in 20% ethyl acetate/hexane and filtered to remove insoluble hydrazine bis(isopropyl)carbamate. Concentration of the filtrate and drying in vacuo afforded 4.3 g (75%) of 24 as a white solid. $^1$H NMR, (DMSO-d6): δ 8.09 (s, 1H), 7.4-7.2 (m, 5H), 6.85 (s, 2H), 4.36 (s, 2H), 4.19 (m, 1H), 4.06 (m, 1H), 3.96 (m, 1H), 3.38 (m, 2H), 2.33 (m, 1H), 1.16 (d, J=6 Hz, 3H), 0.85 (s, 9H), 0.17 (s, 3H), 0.00 (s, 3H).

Example 21

(2R,3R)-1-Benzyloxy-2-((2-amino-1,6-dihydro-6-oxopurin-9-yl)methyl)butan-3-ol (25)

A solution of 24 (4.3 g, 9.03 mmol) in a mixture of TFA (60 ml) and water (20 ml) was kept at room temperature for 2 days until almost no starting 24 was seen by HPLC analysis. The reaction was concentrated, co-evaporated with acetionitrile (3×100 ml) to remove most of TFA and water and re-dissolved in THF (100 ml), triethylamine (2 ml) was added to neutralize residual TFA followed by 12 ml of 1 M tetrabutylammonium fluoride in THF. The reaction was allowed to proceed for 2 hrs (monitored by HPLC), concentrated and treated with water (70 ml) and ethyl acetate. At this point crystallization of 25 started as a gelatinous solid. After being allowed the solid to form for several hours the mixture was filtered to collect the solid, which was washed with 33% ethyl acetate in hexane and dried to afford 1.65 g of 25. The aqueous phase was extracted with ethyl acetate. All ethyl acetate extracts, including the very first one, were combined, concentrated and chromatographed on silica in a gradient of MeOH (10-20%) in dichloromethane to afford 0.75 g of 25 (combined yield—2.4 g, 77%). $^1$H NMR (DMSO-d6): δ 10.53 (s, 1H), 7.57 (s, 1H), 7.30 (m, 5H), 6.42 (s, 2H), 4.80 (d, J=4.8 Hz, 1H), 4.36 (d, J=1.5 Hz, 2H), 4.11 (m, 1H), 3.99 (m, 1H), 3.67 (m, 1H), 3.32 (m, 2H), 2.10 (m, 1H), 1.09 (d, J=6.3 Hz, 3H).

Example 22

(2R,3R)-1-Benzyloxy-2-((2-(N,N-dimethylformamidino)-1,6-dihydro-6-oxopurin-9-yl)methyl)butan-3-ol (26)

A solution of 25 (0.65 g, 1.9 mmol) in 150 ml of MeOH was hydrogenated at 60 psi in the presence of 0.4 10% Pd/C for 3 days. The reaction was filtered through Celite to remove the catalyst and then concentrated. The resulting solid was re-suspended in ethyl acetate, collected by filtration and dried in vacuo to afford 0.42 g (87%) of 26 as an off-white solid. $^1$H NMR (DMSO-d6): δ 10.54 (s, 1H), 7.61 (s, 1H), 6.46 (s, 2H), 4.73 (d, J=4.8 Hz, 1H), 4.59 (t, J=5 Hz, 1H), 4.10 (m, 1H), 3.96 (m, 1H), 3.63 (m, 1H), 3.25 (m, 2H), 1.83 (m, 1H), 1.10 (d, J=6.3 Hz, 3H).

Example 23

(2R,3R)-2-((2-(N,N-dimethylformamidino)-1,6-dihydro-6-oxopurin-9-yl)methyl)butane-1,3-diol (27)

To a suspension of 26 (0.41 g, 1.61 mmol) in 6 ml of anhydrous DMF was added 0.6 ml (4.5 mmol) N,N-dimethylformamide dimethyl acetal. The reaction was stirred for several minutes before clear solution was obtained. The reaction was allowed to proceed for 5 hrs, concentrated, co-evaporated twice with xylene and re-dissolved in MeOH (15 ml). After being kept at room temperature for 1 hrs, the reaction was concentrated on a rotary evaporator. The resulting material was dried by co-evaporation with MeOH and ethyl acetate until white solid (0.5 g, 100%) was obtained. $^1$H NMR (DMSO-d6): δ 11.20 (s, 1H), 8.52 (s, 1H), 7.74 (s, 1H), 4.69 (d, J=4.8 Hz, 1H), 4.60 (t. J=5 Hz, 1H), 4.16 (m, 1H), 4.01 (m, 1H), 3.69 (m, 1H), 3.37 (m, 1H), 3.27 (m, 1H), 3.14 (s, 3H), 3.03 (s, 3H), 1.87 (m, 1H), 1.14 (d, J=6.3 Hz, 3H).

Example 24

(2R,3R)-1-(Bis(4-methoxyphenyl)(phenyl)methoxy)-2-((2-N,N-dimethylformamidino)-1,6-dihydro-6-oxopurin-9-yl)methyl)butan-3-ol (28)

DMTCl (0.62 g, 1.8 mmol) was added to a solution of 27 (0.5 g, 1.6 mmol) in 20 ml of anhydrous pyridine. The reaction was stirred at room temperature overnight, quenched with MeOH (2 mL), concentrated in vacuo and partitioned between ethyl acetate and 10% citric acid. The organic phase was washed with saturated NaCl dried over Na$_2$SO$_4$ and concentrated. The resultant material was chromatographed on silica eluting with a gradient of MeOH (10-15%) in ethyl acetate. Concentration of the product-containing fractions afforded 0.76 g (78%) of 28 as a white amorphous solid. $^1$H NMR (DMSO-d6): δ 11.24 (s, 1H), 8.42 (s, 1H), 7.67 (s, 1H), 7.22 (m, 5H), 7.11 (m, 4H), 6.77 (d, J=8.1 Hz, 4H), 4.72 (d, J=4.8 Hz, 1H), 4.17 (m, 2H), 3.75 (m, 1H), 3.72 (s, 6H), 3.05 (m, 1H), 3.01 (s, 3H), 2.96 (s, 3H), 2.89 (m, 1H), 2.18 (m, 1H), 0.99 (d, J=6.3 Hz, 3H).

Example 25

(2R,3R)-1-(Bis(4-methoxyphenyl)(phenyl)methoxy)-2-((2-(N,N-dimethylformamidino)-1,6-dihydro-6-oxopurin-9-yl)methyl)butan-3-yl 2-cyanoethyl N,N-diisopropylphosphoramidite (29)

To a stirred solution of 28 (0.75 g, 1.22 mmol) in 20 ml of anhydrous dichloromethane was added diisopropylammonium tetrazolide (0.26 g) followed by 0.66 g (2.19 mmol) of 2-cyanoethyl N,N,N',N'-tetraisopropylphosphordiamidite. After being stirred at room temperature for 20 hrs the reaction was concentrated, and the residue portioned between ethyl acetate and saturated NaHCO$_3$. The organic phase was washed with saturated NaCl, dried over Na$_2$SO$_4$ and concentrated in vacuo. The crude phosphoramidite was precipitated twice by re-dissolving in small (~10 ml) amount of ethyl acetate, diluting with hexane (100 ml), allowing precipitate as an oil and decanting the liquid. Drying in vacuo afforded 0.95 g (96%) of 29 as an amorphous white solid. $^{31}$P NMR (DMSO-d6): δ 146.97, 145.66.

Example 26

(2S,3R)-(2-(Benzyloxy)methyl)-3-(tert-butyl)dimethylsiloxy)butoxy)(tert-butyl)dimethylsilane (30)

To a solution of 4 (17.9 g, 55.3 mmol) in 200 ml of anhydrous DMF was added imidazole (5.3 g) followed by tert-butyldimethylsilyl chloride (10.6 g, 70.3 mmol). The reaction was kept at room temperature for 2 h and concentrated on a rotary evaporator to an oil. The oil was partitioned between water (200 ml) and ethyl acetate (300 ml). The organic phase was washed with water, saturated NaCl, and dried over MgSO$_4$. The crude product obtained after concentration of the extract was chromatographed on silica (~600 g) eluting with 0 to 5% ethyl acetate in hexane to afford 23.4 g (96%) of 30 as a colorless liquid. $^1$H NMR (CDCl$_3$): δ 7.27 (m, 5H), 4.45 (d, J=1.5 Hz, 2H), 4.02 (m, 1H), 3.72 (m, 1H), 3.62 (m, 1H), 3.48 (m, 2H), 1.81 (m, 1H), 1.09 (d, J=6.3 Hz, 3H), 0.85 (s, 9H), 0.83 (s, 9H), 0.00 (s, 12H).

Example 27

(2S,3R)-2-((tert-Butyl)dimethylsiloxy)methyl)-3-((tert-butyl)dimethylsiloxy)butan-1-ol (31)

A solution of 30 (4.5 g, 10.2 mmol) in 100 ml of anhydrous ethanol was hydrogenated at 60 psi in the presence of 10% Pd/C for 3 hrs. The catalyst was removed by filtration through Celite and washed with ethanol. The filtrate was concentrated, co-evaporated with ethyl acetate to remove residual ethanol and dried in vacuo to afford 3.4 g (96%) of 31 as a colorless oil. $^1$H NMR (DMSO-d6): δ 4.28 (t, J=5 Hz, 1H), 3.96 (m, 1H), 3.62 (m, 2H), 3.41 (m, 1H), 3.33 (m, 1H), 1.52 (m, 1H), 1.08 (d, J=6.3 Hz, 3H), 0.84 (s, 9H), 0.83 (s, 9H), 0.00 (s, 12H).

Example 28

(2S,3R)-1,3-Bis((tert-Butyl)dimethylsiloxy)-2-((3-benzoyl-3,4-dihydro-5-methyl-2,4-dioxopyrimidin-1(2H)-yl)methyl)butane (32)

To a cold (ice/water bath) solution of 31 (1.7 g, 4.9 mmol), 3-benzoylthymine (1.5 g, 6.5 mmol) and triphenylphosphine (1.71 g, 6.5 mmol) in 50 ml of anhydrous THF was added dropwise via syringe with stirring 1.26 ml (6.5 mmol) of diisopropylazodicarboxylate. The reaction was removed from the bath and stirred at room temperature for 15 hrs and then concentrated. The reaction was diluted with ethyl acetate (~10 ml) to precipitate some of triphenylphosphine oxide and the DIPADC by-product. The solids were filtered off and the filtrate concentrated. The resultant crude product, which still contained some Ph$_3$PO, was chromatographed on silica eluting with 10% ethyl acetate in hexane. Concentration of the pure product fractions afforded 1.9 g (69%) of 32 as a colorless viscous syrup. $^1$H NMR (DMSO-d6): δ 7.89 (d, J=6.9 Hz, 2H), 7.77 (t, J=7.5 Hz, 1H), 7.67 (d, J=1 Hz, 1H), 7.57 (t, J=8.1 Hz, 2H), 3.99 (m, 1H), 3.80 (m, 1H), 3.60 (m, 3H), 2.07 (m, 1H), 1.81 (s, 3H), 1.12 (d, J=6.3 Hz, 3H), 0.84 (s, 9H), 0.83 (s, 9H), 0.01 (s, 6H), 0.00 (s, 6H).

Example 29

(2S,3R)-2-((3,4-Dihydro-5-methyl-2,4-dioxopyrimidin-1(2H)-yl)methyl)butane-1,3-diol (33)

To a solution of 32 (1.9 g, 3.38 mmol) in 20 ml of THF was added 6 ml of 1 M TBAF in THF. After being kept at room temperature for 2 hrs the reaction was diluted with methanol (100 ml), water (100 ml) and treated with 10 ml of 1 M NaOH. The reaction was allowed to proceed overnight, then combined with 10 g of Dowex 66 and 20 g of Dowex 50 w×8×200 and stirred for 1 h. The resin was removed by filtration, washed with 50% methanol and the combined filtrates concentated to afford 0.6 g (77%) of 33 as a white solid. This material contained some impurities but was considered to be pure enough for further use without additional purification.

Example 30

(2S,3R)-1-(Bis(4-methoxyphenyl)(phenyl)methoxy)-2-((3,4-dihydro-5-methyl-2,4-dioxopyrimidin-1(2H)-yl)methyl)butan-3-ol (34)

To a stirred solution of 33 (0.6 g. 2.6 mmol) in 20 ml of anhydrous pyridine was added 0.9 g (2.66 mmol) of DMTCl. After being stirred at room temperature for 5 hrs the reaction was quenched with methanol (3 ml), concentrated and portioned between 10% citric acid and ethyl acetate. The organic phase was washed with saturated NaCl, dried over Na$_2$SO$_4$ and concentrated in vacuo to a solid foam. The crude product was chromatographed on silica eluting with ethyl acetate to afford 0.95 g (69%) of 34 as an amorphous white solid. $^1$H NMR (DMSO-d6): δ 11.16 (s, 1H), 7.28 (m, 6H), 7.21 (m, 4H), 6.85 (m, 4H), 4.59 (d, J=5 Hz, 1H), 3.76 (m, 2H), 3.74 (s, 6H), 3.57 (m, 1H), 3.10 (m, 1H), 2.95 (m, 1H), 2.11 (m, 1H), 1.67 (s, 3H), 1.02 (d, J=6.3 Hz, 3H).

Example 31

(2S,3R)-1-(Bis(4-methoxyphenyl)(phenyl)methoxy)-2-((3,4-dihydro-5-methyl-2,4-dioxopyrimidin-1(2H)-yl)methyl)butan-3-yl 2-cyanoethyl N,N-diisopropylphosphoramidite (35)

To a stirred solution of 34 (0.95 g, 1.79 mmol) in 25 ml of anhydrous dichloromethane was added diisopropylammonium tetrazolide (0.25 g) followed by 0.7 g (2.32 mmol) of 2-cyanoethyl N,N,N',N'-tetraisopropylphosphordiamidite. After being stirred at room temperature for 18 hrs the reaction was concentrated, and the residue portioned between ethyl acetate and saturated NaHCO$_3$. The organic phase was washed with saturated NaCl, dried over Na$_2$SO$_4$ and concentrated in vacuo. The crude phosphoramidite was precipitated twice by re-dissolving in small (~15 ml) amount of ethyl acetate, diluting with hexane (100 ml), allowing to settle as an oil and decanting the liquid. Drying in vacuo afforded 0.95 g (72%) of 35 as an amorphous white solid. $^{31}$P NMR (DMSO-d6): δ 145.81, 144.94.

Example 32

(2S,3R)-1,3-Bis((tert-Butyl)dimethylsiloxy)-2-((2-amino-6-chloro-9H-purin-9-yl)methyl)butane (36)

To a cold (~0° C., ice/water bath) partial solution of 2-amino-6-chloropurine (0.89 g, 5.26 mmol), 31 (1.7 g, 4.87 mmol) and triphenylphosphine (1.5 g, 5.7 mmol) was added dropwise with stirring 1.25 ml (6.4 mmol) of diisopropylazodicarboxylate. The reaction was stirred at room temperature overnight and concentrated. The residue was co-evaporated with xylene to remove residual DMF and chromatographed on silica eluting with 20% to 25% ethyl acetate in hexane. Concentration of the pure product fractions afforded 1.8 g (74%) of 36 as a white solid, $^1$H NMR (DMSO-d6): δ 8.05 (s, 1H), 6.76 (s, 2H), 4.08 (m, 1H), 3.98 (m, 2H), 3.56 (m, 2H), 2.31 (m, 1H), 1.16 (d, J=6.3 Hz, 3H), 0.81 (s, 9H), 0.78 (s, 9H), 0.00 (s, 3H), –0.025 (s, 3H), –0.095 (s, 3H), –0.10 (s, 3H).

Example 33

(2S,3R)-2-((2-Amino-1,6-dihydro-6-oxopurin-9-yl)methyl)butane-1,3-diol (37)

A solution of 36 (1.8 g, 3.6 mmol) in a mixture of TFA (60 ml) and water (20 ml) was kept at room temperature for 2 days until almost no starting material was found by HPLC analysis. The reaction was concentrated, co-evaporated with water (3×100 ml) and re-dissolved in ~5 ml of acetonitrile. Ethyl ether (~50 ml) was added to precipitate 0.84 g of 37 as a TFA salt. The salt was dissolved in ~7 ml of ethanol, treated with 0.5 ml of triethylamine and allowed to crystallize at –20° C. for 2 hrs. The crystals were collected by filtration, washed with ethyl ether and dried in vacuo to afford 0.64 g (70%) of 37 as a white solid. $^1$H NMR (DMSO-d6): δ 10.55 (s, 1H), 7.63 (s, 1H), 6.46 (s, 2H), 4.63 (d, J=5 Hz, 1H), 4.55 (t, J=5 Hz, 1H), 3.97 (d, J=7.5 Hz, 2H), 3.64 (m, 1H), 3.41 (m, 2H), 1.92 (m, 1H), 1.10 (d, J=6.3 Hz, 3H).

Example 34

(2S,3R)-2-((2-(N,N-Dimethylformamidino)-1,6-dihydro-6-oxopurin-9-yl)methyl)butane-1,3-diol (38)

To a suspension of 37 (0.64 g, 2.5 mmol) in 10 ml of anhydrous DMF was added 1.0 ml (7.5 mmol) of N,N-dimethylformamide dimethyl acetal. A clear solution was obtained after about 5 min of stirring. The solution was kept at room temperature for 3 hrs and concentrated in vacuo to an oil, which was then re-dissolved in 25 ml of methanol and left at room temperature overnight. The reaction was concentrated and dried in vacuo to afford 0.78 g (100%) of 38 as a white solid, which contained some residual DMF. $^1$H NMR (DMSO-d6): δ 11.12 (br s, 1H), 8.52 (s, 1H), 7.73 (s, 1H), 4.62 (d, J=5 Hz, 1H), 4.54 (t, J=5 Hz, 1H), 4.05 (d, J=6.6 Hz, 2H), 3.66 (m, 1H), 3.43 (m, 2H), 3.13 (s, 3H), 3.02 (s, 3H), 1.95 (m, 1H), 1.11 (d, J=6.3 Hz, 3H).

Example 35

(2S,3R)-1-(Bis(4-methoxyphenyl)(phenyl)methoxy)-2-((2-(N,N-dimethylformamidino)-1,6-dihydro-6-oxopurin-9-yl)methyl)butan-3-ol (39)

DMTCl (1.0 g, 2.96 mmol) was added to a solution of 38 (0.78 g. 2.5 mmol) in 30 ml of anhydrous pyridine. The reaction was stirred at room temperature overnight, quenched with MeOH (2 mL), concentrated in vacuo and partitioned between ethyl acetate and 10% citric acid. The organic phase was washed with saturated NaCl dried over Na$_2$SO$_4$ and concentrated. The resultant material was chromatographed on silica eluting with a gradient of MeOH (10-15%) in ethyl acetate. Concentration of the product-containing fractions afforded 1.15 g (75%) of 39 as a white amorphous solid. $^1$H NMR (DMSO-d6): δ 11.24 (s, 1H), 8.41 (s, 1H), 7.64 (s, 1H), 7.26 (m, 5H), 7.14 (m, 4H), 6.79 (m, 4H), 4.66 (d, J=5 Hz, 1H), 4.20 (m, 1H), 4.03 (m, 1H), 3.74 (m, 1H), 3.71 (s, 6H), 3.12 (m, 1H), 3.00 (s, 3H), 2.94 (m, 1H), 2.88 (s, 3H), 2.26 (m, 1H), 1.00 (d, J=6.3 Hz, 3H).

Example 36

(2S,3R)-1-(Bis(4-methoxyphenyl)(phenyl)methoxy)-2-((2-(N,N-dimethylformamidino)-1,6-dihydro-6-oxopurin-9-yl)methyl)butan-3-yl 2-cyanoethyl N,N-diisopropylphosphoramidite (40)

To a stirred solution of 39 (1.1 g, 1.8 mmol) in 30 ml of anhydrous dichloromethane was added diisopropylammonium tetrazolide (0.3 g) followed by 0.78 g (2.6 mmol) of 2-cyanoethyl N,N,N',N'-tetraisopropylphosphordiamidite. After being stirred at room temperature for 20 hrs the reaction was concentrated, and the residue portioned between ethyl acetate and saturated NaHCO$_3$. The organic phase was washed with saturated NaCl, dried over Na$_2$SO$_4$ and concentrated in vacuo. The crude phosphoramidite was p twice by re-dissolving in small (~10 ml) amount of ethyl acetate, diluting with hexane (100 ml), allowing precipitate as an oil and decanting the liquid. Drying in vacuo afforded 1.1 g (75%) of 40 as an amorphous white solid. $^{31}$P NMR (DMSO-d6): δ 146.17, 144.42.

Example 37

(2S,3R)-1,3-Bis((tert-butyl)dimethylsiloxy)-2-((3-benzoyl-3,4-dihydro-2,4-dioxopyrimidin-1(2H)-yl)methyl)butane (41)

To a cold (ice/water bath) solution of 31 (6.6 g. 18.9 mmol), 3-benzoyluracyl (4.9 g, 22.7 mmol) and triphenylphosphine (7.2 g, 27.5 mmol) in 100 ml of anhydrous THF was added dropwise via syringe with stirring (5.5 ml, 27.9 mmol) of diisopropylazodicarboxylate. The reaction was removed from the bath and stirred at room temperature for 3 hrs and then concentrated. The residue was dried by co-evaporation with xylene and chromatographed on silica eluting with a gradient of ethyl acetate (10-20%) in hexane. Concentration of the product-containing fractions afforded 8.7 g (84%) of 41 as a colorless oil. $^1$H NMR (DMSO-d6): δ 7.92 (d, J=8.1 Hz, 2H), 7.78 (m, 2H), 7.59 (t, J=8.1 Hz, 2H), 5.84 (d, J=7.8 Hz, 1H), 4.01 (m, 1H), 3.84 (m, 1H), 3.69 (m, 1H), 3.59 (m, 2H), 2.08 (m, 1H), 1.12 (d, J=6 Hz, 3H), 0.85 (s, 18H), 0.02 (s, 12H).

Example 38

(2S,3R)-1,3-Bis((tert-butyl)dimethylsiloxy)-2-((3,4-dihydro-2,4-dioxopyrimidin-1(2H)-yl)methyl)butane (42)

Sodium methoxide, 25% in MeOH (6 ml) was added to asolution of 41 (8.7 g, 15.9 mmol) in 300 ml of MeOH. The reaction was stirred at 50° C. for 3 hrs, then treated with 5.3 g of solid triethylammonium chloride and concentrated. The obtained residue was partitioned between water and ethyl acetate. The organicphase was washed with saturated NaCl and dried over Na2SO4. Concentration of the extract gave an oil. The oil was chromatographed on silica eluting with 20 to 30% ethyl acetate in hexane to afford a crude product, which was re-crystallized from hexane (~30 ml) at –20° C. to yield 5.4 g (76%) of 42 as white crystals. $^1$H NMR (DMSO-d6): δ

11.18 (s, 1H), 7.49 (d, J=7.5 Hz, 1H), 5.51 (d, J=7.5 Hz, 1H), 3.99 (m, 1H), 3.75 (m, 1H), 3.55 (m, 3H), 2.03 (m, 1H), 1.12 (d, J=6 Hz, 3H), 0.84 (s, 18H), 0.02 (s, 6H), 0.00 (s, 6H).

Example 39

(2S,3R)-1,3-Bis((tert-butyl)dimethylsiloxy)-2-((2-oxo-4-(1H-1,2,4-triazol-1-yl)pyrimidin-1(2H)-yl)methyl)butane (43)

To a cold (ice/water bath) solution of 42 (2.7 g, 6.08 mmol) and 1,2,4-triazole (5.8 g, 84 mmol) in 37 ml of anhydrous pyridine was added dropwise over 5 min 4.2 g (17.11 mmol) of 4-chlorophenyldichlorophosphate (via syringe). The reaction was allowed to warm up and kept at room temperature for 3 days. The reaction was concentrated and partitioned between ethyl acetate (150 ml) and water (150 ml). The organic phase was washed with 10% citric acid, saturated NaCl and dried over $Na_2SO_4$. The crude material (brown oil) obtained after concentration of the extract was chromatographed on silica eluting with a gradient of ethyl acetate (50-66%) in hexane. Concentration of the pure product fractions afforded 2.0 g (66%) of 43 as a light tan solid. $^1$H NMR (DMSO-d6): δ 9.40 (s, 1H), 8.38 (s, 1H), 8.37 (d, J=7 Hz, 1H), 6.90 (d, J=7 Hz, 1H), 4.05 (m, 2H), 3.83 (m, 1H), 3.60 (d, J=6.3 Hz, 2H), 2.22 (m, 1H), 1.15 (d, J=6 Hz, 3H), 0.81 (s, 9H), 0.79 (s, 9H), 0.01 (s, 6H), −0.04 (s, 6H).

Example 40

(2S,3R)-1,3-Bis((tert-butyl)dimethylsiloxy)-2-((4-amino-2-oxo-pyrimidin-1(2H)-yl)methyl)butane (44)

A solution of 43 (2.0 g, 4.05 mmol) in 60 ml of 6 M $NH_3$/MeOH was heated at 100° C. in a Parr bomb for 2 days. The reaction was cooled, concentrated and chromatographed on silica eluting, first, with ethyl acetate and, second, with 5% MeOH in ethyl acetate. Concentration of the product-containing fractions afforded 1.2 g (67%) of 44 as a white solid. $^1$H NMR (DMSO-d6): δ 7.39 (d, J=7 Hz, 1H), 6.94 (br s, 2H), 5.60 (d, J=7 Hz, 1H), 4.00 (m, 1H), 3.65 (m, 1H), 3.53 (m, 3H), 2.02 (m, 1H), 1.13 (d, J=6 Hz, 3H), 0.86 (s, 9H), 0.84 (s, 9H), 0.04 (s, 6H), −0.01 (s, 3H), −0.02 (s, 3H).

Example 41

(2S,3R)-2-((4-Amino-2-oxo-pyrimidin-1(2H)-yl)methyl)butane-1,3-diol (45)

To a solution of 44 (1.2 g. 2.7 mmol) in 15 of anhydrous DMF was added triethylamine (0.45 ml) followed by 0.31 ml (3.3 mmol) of acetic anhydride. The reaction was kept at room temperature for 1 day, then 3 hrs at 50 C and concentrated. The oily residue was dried by co-evaporation with xylene and then re-dissolved in ethyl acetate. The solution was washed with saturated $NaHCO_3$ (2×100 ml), saturated NaCl, dried over $MgSO_4$. Concentration of the extract and drying in vacuo afforded 1.3 g (99%) of 45 as an off-white amorphous solid. $^1$H NMR (DMSO-d6): δ 10.79 (s, 1H), 7.94 (d, J=7 Hz, 1H), 7.12 (d, J=7 Hz, 1H), 4.01 (m, 1H), 3.87 (m, 1H), 3.69 (m, 1H), 3.56 (d, J=6 Hz, 2H), 2.14 (m, 1H), 2.08 (s, 3H), 1.14 (d, J=6 Hz, 3H), 0.84 (s, 9H), 0.82 (s, 9H), 0.02 (s, 6H), −0.02 (s, 3H), −0.03 (s, 3H).

Example 42

(2S,3R)-2-((4-Acetamido-2-oxo-pyrimidin-1(2H)-yl)methyl)butane-1,3-diol (46)

To a solution of 45 (1.3 g, 2.7 mmol) in 38 ml of THF was added 2.3 ml of 1M TBAF in THF. The reaction was stirred for 24 hrs, concentrated and chromatographed on silica eluting with, first, 10% MeOH in dichloromethane and, second, with 15% MeOH in dichloromethane. Concentration of the pure product fractions afforded 0.5 g (72%) of 46 as white amorphous solid. $^1$H NMR (DMSO-d6): δ10.81 (s, 1H), 7.98 (d, J=7 Hz, 1H), 7.12 (d, J=7 Hz, 1H), 4.58 (d, J=5 Hz, 1H), 4.48 (t, J=5 Hz, 1H), 3.82 (d, J=7 Hz, 2H), 3.67 (m, 1H), 3.46 (m, 1H), 3.38 (m, 1H), 2.09 (s, 3H), 1.89 (m, 1H), 1.09 (d, J=6 Hz, 3H).

Example 43

(2S,3R)-1-(Bis(4-methoxyphenyl)(phenyl)methoxy)-2-((4-acetamido-2-oxo-pyrimidin-1(2H)-yl)methyl)butan-3-ol (47)

DMTCl (0.79 g, 2.34 mmol) was added to a stirred solution of 46 (0.5 g, 1.96 mmol) in 20 ml of anhydrous pyridine. After being stirred at room temperature overnight the reaction was quenched with MeOH (2 ml) and concentrated to an oil. The oil was partition between dichloromethane and 10% citric acid. The organic phase was washed with saturated NaCl, dried over $Na_2SO_4$ and concentrated. The resulting material was chromatographed on silica eluting with a gradient of methanol (5-7.5%) in ethyl acetate. Concentration of the pure product fractions afforded 0.99 g (90%) of 47 as a white amorphous solid. $^1$H NMR (DMSO-d6): δ 10.78 (s, 1H), 7.73 (d, J=7 Hz, 1H), 7.27 (m, 5H), 7.16 (m, 4H), 6.98 (d, J=7 Hz, 1H), 6.82 (m, 4H), 4.60 (d, J=5 Hz, 1H), 3.84 (d, J=7 Hz, 2H), 3.76 (m, 1H), 3.72 (s, 6H), 3.08 (m, 1H), 2.99 (m, 1H), 2.20 (m, 1H), 2.09 (s, 3H), 1.03 (d, J=6 Hz, 3H).

Example 44

(2S,3R)-1-(Bis(4-methoxyphenyl)(phenyl)methoxy)-2-((4-acetamido-2-oxo-pyrimidin-1(2H)-yl)methyl)butan-3-yl 2-cyanoethyl N,N-diisopropylphosphoramidite (48)

To a stirred solution of 47 (0.98 g, 1.75 mmol) in 30 ml of anhydrous dichloromethane was added diisopropylammonium tetrazolide (0.3 g) followed by 0.8 g (2.66 mmol) of 2-cyanoethyl N,N,N',N'-tetraisopropylphosphordiamidite. After being stirred at room temperature for 20 hrs the reaction was concentrated, and the residue portioned between ethyl acetate and saturated $NaHCO_3$. The organic phase was washed with saturated NaCl, dried over $Na_2SO_4$ and concentrated in vacuo. The crude phosphoramidite was p twice by re-dissolving in small (~10 ml) amount of ethyl acetate, diluting with hexane (100 ml), allowing precipitate as an oil and decanting the liquid. Drying in vacuo afforded 1.1 g (83%) of 48 as an amorphous white solid. $^{31}$P NMR (DMSO-d6): δ 145.84, 144.94.

Example 45

(2S,3R)-1,3-Bis((tert-butyl)dimethylsiloxy)-2-((6-chloro-9H-purin-9-yl)methyl)butane (49)

To a cold (~0° C., ice/water bath) partial solution of 6-chloropurine (2.2 g, 14.2 mmol), 31 (4.1 g, 11.76 mmol) and triphenylphosphine (4.8 g, 18.3 mmol) was added dropwise with stirring 3.6 ml (18.3 mmol) of diisopropyl azodicarboxylate. The reaction was stirred at room temperature for 4 hrs and concentrated. The residue was co-evaporated with xylene to remove residual DMF and chromatographed on silica eluting with 10% to 20% ethyl acetate in hexane. Concentration of the pure product fractions afforded 4.2 g (73%) of 49 as a viscous oil. $^1$H NMR DMSO-d6): δ 8.75 (s, 1H), 8.66 (s, 1H), 4.38 (m, 1H), 4.25 (m, 1H), 4.03 (m, 1H), 3.58 (m, 2H), 2.40 (m, 1H), 1.10 (d, J=6 Hz, 3H), 0.74 (s, 9H), 0.73 (s, 9H), −0.06 (s, 6H), −0.13 (s, 6H).

Example 46

(2S,3R)-1,3-Bis((tert-butyl)dimethylsiloxy)-2-((6-amino-9H-purin-9-yl)methyl)butane (50)

A solution of 49 (4.2 g. 8.65 mmol) in 60 ml of 6M NH$_3$/MeOH was sealed in a 100 ml Parr bomb and heated with stirring for 20 hrs. The reaction was cooled and concentrated to a white solid, which was re-crystallized from 10% ethyl acetate/hexane to afford 2.7 g (67%) of 50 as white crystals. $^1$H NMR (DMSO-d6): δ 8.10 (s, 1H), 8.02 (s, 1H), 7.16 (s, 2H), 4.18 (m, 1H), 4.06 (m, 1H), 4.00 (m, 1H), 3.53 (m, 2H), 2.29 (m, 1H), 1.16 (d, J=6 Hz, 3H), 0.84 (s, 9H), 0.79 (s, 9H), 0.01 (s, 6H), −0.10 (s, 6H).

Example 47

(2S,3R)-1,3-Bis((tert-butyl)dimethylsiloxy)-2-((6-benzamido-9H-purin-9-yl)methyl)butane (51)

To a cold (~0 C, ice/water bath) solution of 50 (2.65 g, 5.7 mmol) in 50 ml of anhydrous pyridine was added dropwise with stirring 1.0 ml (8.6 mmol) of benzoyl chloride (via a syringe). The reaction was allowed to warm up to room temperature, stirred for about 5 hrs until no starting material was found by HPLC analysis, and then treated with 10 ml of 6M NH$_3$/MeOH. After being stirred for about 3 hrs and no more of the bis-benzoylated intermediate found by HPLC, the reaction was concentrated, re-suspended in dichloromethane (~50 ml) and filtered to remove poorly insoluble benzamide. The filtrate was concentrated, washed with 10% citric acid, saturated NaCl, dried over Na$_2$SO$_4$ and concentrated again. The crude product was crystallized from 50% ethyl acetate/hexane (~20 ml) to afford 2.4 g (74%) of 51 as white crystals. $^1$H NMR (DMSO-d6): δ 11.15 (s, 1H), 8.70 (s, 1H), 8.40 (s, 1H), 8.02 (d, J=7.2 Hz, 2H), 7.63 (m, 1H), 7.54 (t, J=7.8 Hz, 2H), 4.33 (m, 1H), 4.21 (m, 1H), 4.04 (m, 1H), 3.58 (m, 2H), 2.38 (m, 1H), 1.19 (d, J=6 Hz, 3H), 0.84 (s, 9H), 0.79 (s, 9H), 0.01 (s, 3H), 0.00 (s, 3H), −0.10 (s, 6H).

Example 48

(2S,3R)-2-((4-Benzamido-9H-purin-9-yl)methyl)butane-1,3-diol (52)

To a solution of 51 (2.38 g, 4.18 mmol) in 60 ml of THF was added 3.7 ml of 1M TBAF in THF. The reaction was stirred for 24 hrs, concentrated and chromatographed on silica eluting with, first, 10% MeOH in dichloromethane and, second, with 15% MeOH in dichloromethane. Concentration of the pure product fractions afforded 1.2 g (84%) of 52 as white amorphous solid. $^1$H NMR (DMSO-d6): δ 11.14 (s, 1H), 8.74 (s, 1H), 8.42 (s, 1H), 8.04 (d, J=7.2 Hz, 2H), 7.65 (m, 1H), 7.55 (t, J=7.8 Hz, 2H), 4.69 (d, J=5 Hz, 1H), 4.59 (t, J=5 Hz, 1H), 4.32 (d, J=7.2 Hz, 2H), 3.68 (m, 1H), 3.45 (m, 2H), 2.13 (m, 1H), 1.13 (d, J=6 Hz, 3H).

Example 49

(2S,3R)-1-(Bis(4-methoxyphenyl)(phenyl)methoxy)-2-((6-benzamido-9H-purin-9-yl)methyl)butan-3-ol (53)

DMTCl (0.58 g, 1.71 mmol) was added to a stirred solution of 52 (0.5 g, 1.46 mmol) in 20 ml of anhydrous pyridine. After being stirred at room temperature overnight the reaction was quenched with MeOH (2 ml) and concentrated to an oil. The oil was partition between dichloromethane and 10% citric acid. The organic phase was washed with saturated NaCl, dried over Na$_2$SO$_4$ and concentrated. The resulting material was chromatographed on silica eluting with acetone (30 to 40%) in ethyl acetate. Concentration of the pure product fractions afforded 0.7 g (74%) of 53 as a white amorphous solid. $^1$H NMR (DMSO-d6): δ 11.14 (s, 1H), 8.71 (s, 1H), 8.31 (s, 1H), 8.03 (d, J=7.2 Hz, 2H), 7.65 (m, 1H), 7.56 (t, J=7.8 Hz, 2H), 7.21 (m, 5H), 7.08 (t, J=8.7 Hz, 4H), 6.80 (m, 4H), 4.73 (d, J=5 Hz, 1H), 4.32 (m, 2H), 3.77 (m, 1H), 3.14 (m, 1H), 2.96 (m, 1H), 2.43 (m, 1H), 1.05 (d, J=6 Hz, 3H).

Example 50

(2S,3R)-1-(Bis(4-methoxyphenyl)(phenyl)methoxy)-2-((6-benzamido-9H-purin-9-yl)methyl)butan-3-yl 2-cyanoethyl N,N-diisopropylphosphoramidite (54)

To a stirred solution of 53 (0.7 g, 1.08 mmol) in 20 ml of anhydrous dichloromethane was added diisopropylammonium tetrazolide (0.18 g) followed b) 0.52 g (1.72 mmol) of 2-cyanoethyl N,N,N',N'-tetraisopropylphosphordiamidite. After being stirred at room temperature for 20 hrs the reaction was concentrated, and the residue portioned between ethyl acetate and saturated NaHCO$_3$. The organic phase was washed with saturated NaCl, dried over Na$_2$SO$_4$ and concentrated in vacuo. The crude phosphoramidite was p twice by re-dissolving in small (~10 ml) amount of ethyl acetate, diluting with hexane (100 ml), allowing precipitate as an oil and decanting the liquid. Drying in vacuo afforded 0.9 g (99%) of 54 as an amorphous white solid. $^{31}$P NMR (DMSO-d6): δ 145.96, 145.03.

Example 51

Figure 6:
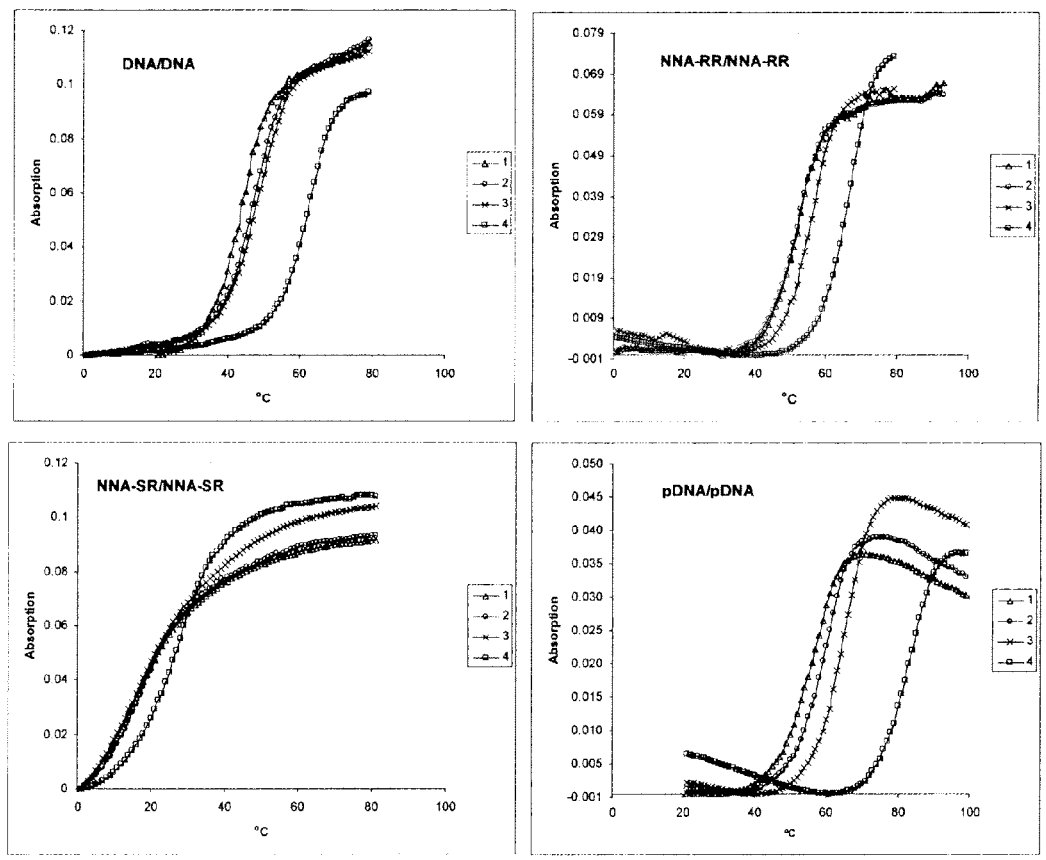
FIG. 6 shows melting curves for matched homoduplexes (fully complementary duplexes with identical nucleic acid backbone) with variable A/T composition.
Figure 9:
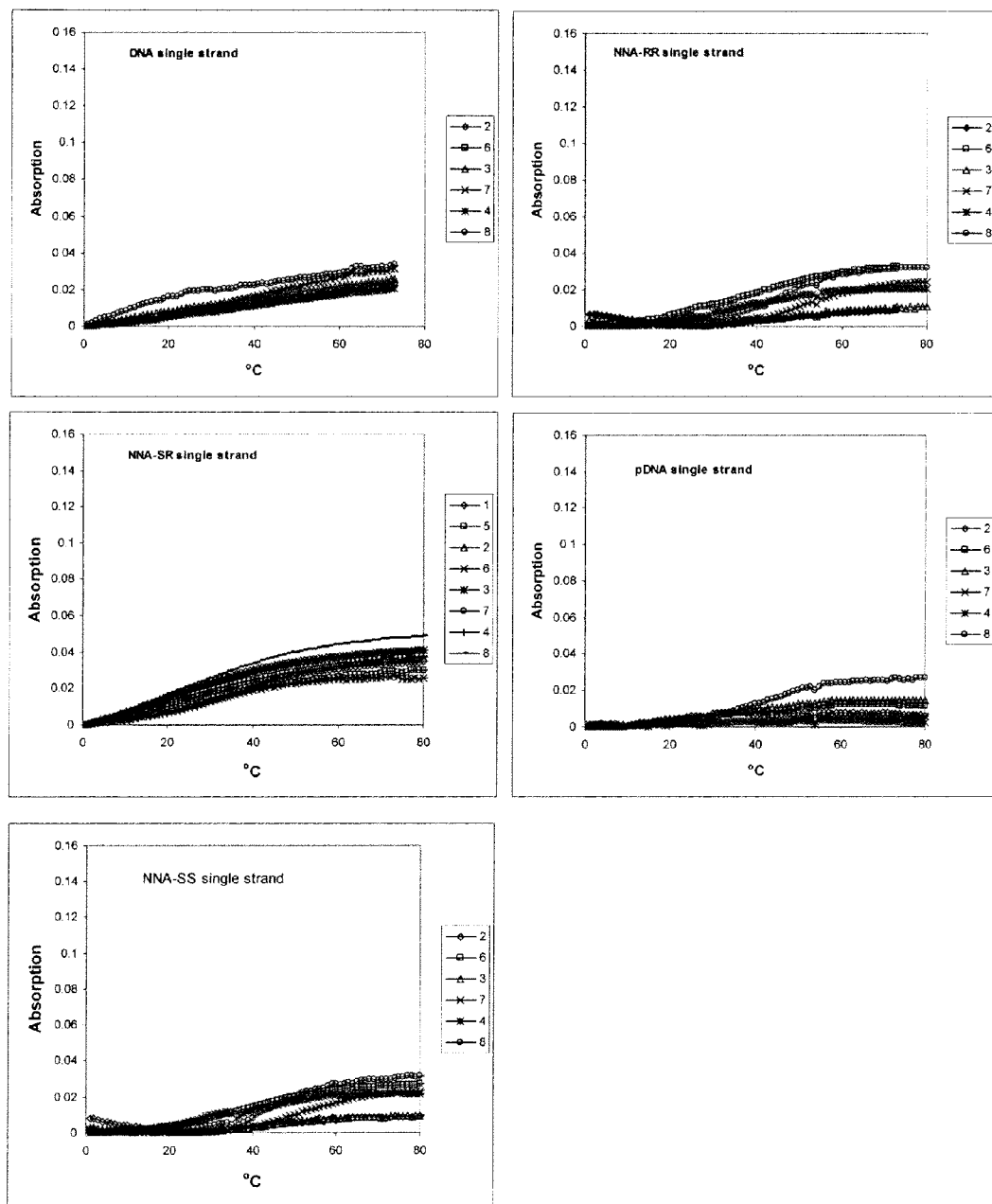
FIG. 9 shows temperature dependence of absorption (268 nm) for various single stranded nucleic acids.

The melting curves of the oligonucleotides of the disclosure were determined as follows: oligonucleotides having the sequences shown in FIG. 6 were combined in equimolar 2 µM concentrations in buffer containing 980 mM NaCl and 20 mM Na-PIPES (pH 7). The solutions in 1 cm cuvettes were brought to 80° C. briefly then the temperature lowered to 15° C. Measurements were conducted on a Cary Bio 400 UV-Vis spectrophotometer equipped with a thermal peltier cell block and temperature probe. The temperature was ramped at a rate of 1° C./min from 15 to >75° C. with the wavelength monitored at 268 nm. Melting curves for matched homoduplexes (fully complementary duplexes with identical nucleic acid backbone of either DNA. R,R stereoisomer of the preferred nucleoside (NNA-RR), S,R stereoisomer of the preferred nucleosides (NNA-SR), or pDNA) with variable A/T composition are shown in FIG. 6. The melting temperature was calculated as the midpoint between the baselines of the associated and dissociated portions of the melting curve. FIG. 7 shows a summary of melting temperatures for the homoduplexes with various nucleic acid backbones and A/T composition defined in FIG. 6. FIG. 8 shows the melting curves for the matched heteroduplexes with NNA-RR and DNA backbones and variable A/T composition defined in FIG. 6. FIG. 9 shows the temperature dependence of absorption (268 nm) for various single stranded nucleic acids defined in FIG. 6.

Example 52

3-Benzoyl-1-((1S,2R,3S)-3-((tert-butyldiphenylsilyl)oxy)-2-((trityloxy)methyl)cyclopentyl)-5-methylpyrimidine-2,4(1H,3H)-dione (56)

Diisopropyl azodicarboxylate (0.396 g, 0.386 ml, 1.96 mmol) was added dropwise over 5 min to a stirred cold (0-3° C.) solution of compound 55 (US Appl. 20110251387) (1.0 g, 1.63 mmol), N3-benzoyl-thymine (0.451 g, 1.96 mmol), and triphenylphosphine (0.514 g, 1.96 mmol) in anhydrous DMF (24 ml). The resultant solution was stirred under argon overnight at room temperature, then concentrated and the obtained residue carefully chromatographed on silica eluting with a gradient (3-5%) of ethyl acetate in dichloromethane to afford 0.49 g (37% yield) of compound 56 as a white solid. $^1$H NMR (DMSO-d6): δ7.75 (bt, J=7.5 Hz, 1H), 7.67 (bd, J=7.7 Hz, 2H), 7.54-7.18 (m, 28H). 5.08 (q, J=7.8, 1H), 4.18 (q, J=6.0 Hz, 1H), 3.06 (dd, J=9.6, J=4.5, 1H), 2.68-2.55 (m, 1H), 2.31 (t, J=9.6, 1H), 2.20-2.10 (m, 1H), 1.95-1.77 (m, 2H), 1.62-1.50 (m, 1H), 1.52 (s, 3H), 0.92 (s, 9H).

Example 53

3-Benzoyl-1-((1S,2R,3S)-3-hydroxy-2-(hydroxymethyl)cyclopentyl)-5-methylpyrimidine-2,4(1H,3H)-dione (57)

Compound 56 (0.45 g, 0.55 mmol) was dissolved in mixture of TFA (15 ml) and water (5 ml). The solution was stirred under argon for 1 h, then concentrated, co-evaporated 2 times with water to remove residual TFA and chromatographed on silica eluting with a gradient (5-7%) of MeOH in dichloromethane to yield nucleoside 57 (0.140 g, 75% yield) as a white solid. $^1$H NMR (DMSO-d6): δ7.95-7.92 (m, 2H), 7.80-7.74 (m, 2H), 7.57 (t, J=7.7 Hz, 2H), 4.96-4.86 (m, 1H), 4.81 (d, J=5.1 Hz, 1H), 4.62 (t, J=4.0, 1H), 3.95-3.88 (m, 1H), 3.50-3.45 (m, 1H), 3.35-3.25 (m, 1H), 2.12-1.98 (m, 4H), 1.86 (s, 3H), 1.48-1.38 (m, 1H).

Example 54

3-Benzoyl-1-((1S,2R,3S)-2-((bis(4-methoxyphenyl)(phenyl)methoxy)methyl)-3-hydroxycyclopentyl)-5-methylpyrimidine-2,4(1H,3H)-dione (58)

Dimethoxytrityl chloride (0.325 g. 0.958 mmol) was added to a solution of nucleoside 57 (0.30 g, 0.871 mmol) in anhydrous pyridine (5 ml); the reaction was stirred overnight at room temperature and then concentrated. The obtained residue was diluted with ethyl acetate, washed twice with 10% citric acid, saturated sodium bicarbonate, brine and dried over MgSO$_4$. The extract was concentrated and the resulting oil chromatographed on silica eluting with a gradient (10-15%) of ethyl acetate in dichloromethane to afford DMT-protected thymidine analogue 58 (0.29 g, 51% yield) as a solid foam. $^1$H NMR (DMSO-d6): δ7.74-7.70 (m, 3H), 7.53-7.43 (m, 3H), 7.37-7.16 (m, 9H), 6.86-6.80 (m, 4H), 5.1-5.0 (m, 1H), 4.96-4.86 (m, 1H), 4.87 (d, J=5.4 Hz, 1H), 4.04-4.00 (m, 1H), 3.72 (s, 3H), 3.71 (s, 3H), 3.14 (dd, J=9.8 Hz, J=4.0 Hz, 1H), 2.40-2.28 (m, 1H), 2.25-1.83 (m, 3H), 1.56 (s, 3H), 1.50-1.40 (m, 1H).

Example 55

(1S,2R,3S)-3-(3-Benzoyl-5-methyl-2,4-dioxo-3,4-dihydropyrimidin-1(2H)-yl)-2-((bis(4-methoxyphenyl)(phenyl)methoxy)methyl)cyclopentyl(2-cyanoethyl)diisopropylphosphoramidite (59)

2-Cyanoethyl N,N,N',N'-tetraisopropylphosphordiamidite (0.189 g, 0.626 mmol) was added to mixture of compound 58 (0.27 g, 0.417 mmol) and diisopropylammonium tetrazolide (0.071 g, 0.417 mmol) in dry DCM (5 ml) under argon. The reaction was stirred overnight then diluted with saturated sodium bicarbonate and extracted with ethyl acetate. The organic phase was separated, washed with brine, dried over Na$_2$SO$_4$, and concentrated. The obtained material was re-precipitated by dissolving in a small amount of ethyl acetate and adding excess hexane followed by decanting the liquid phase. Drying in vacuo afforded phosphoramidite 59 as a light tan viscous oil. $^{31}$P NMR (CDCl$_3$): δ148.12, 147.41.

Example 56

9-((1S,2R,3S)-3-((tert-Butyldiphenylsilyl)oxy)-2-((trityloxy)methyl)cyclopentyl)-6-chloro-9H-purine (60)

Diisopropyl azodicarboxylate (0.726 g, 0.707 ml, 3.59 mmol) was added dropwise over 5 min to a stirred cold (0-3° C.) solution of compound 55 (2.0 g, 13.26 mmol), 6-chloropurine (0.555 g, 3.593 mmol), and triphenylphosphine (0.942 g, 3.59 mmol) in anhydrous DMF (24 ml). The reaction was stirred under argon for 22 h and then concentrated in vacuo. The resultant residue was chromatographed on silica eluting with 20% ethyl acetate in hexane to afford nucleoside 60 (1.24 g, 51% yield) as a white solid. $^1$H NMR (DMSO-d6): δ8.45 (s, 1H), 8.36 (s, 1H), 7.49-7.39 (m, 6H), 7.36-7.20 (m, 4H), 7.15-7.06 (m, 9H), 6.96-6.88 (m, 6H), 5.56-5.47 (m, 1H), 4.43-4.34 (m, 1H), 3.04 (dd, J=9.5, J=4.4, 1H), 2.88-2.82 (m, 1H), 2.38-2.28 (m, 1H), 2.05-1.94 (m, 2H), 1.80-1.67 (m, 2H), 0.94 (s, 9H).

Example 57

9-((1S,2R,3S)-3-((tert-Butyldiphenylsilyl)oxy)-2-((trityloxy)methyl)cyclopentyl)-9H-purin-6-amine (61)

A solution of chloropurine intermediate 60 (1.2 g, 1.6 mmol) in 60 ml of 7 N ammonia in methanol was heated at 100° C. in a Parr bomb for 18 h. The reaction was cooled, concentrated and the residue partitioned between ethyl acetate and water. The organic phase was washed with brine, dried over Na$_2$SO$_4$ and concentrated. The obtained residue was chromatographed on silica eluting with 3% triethylamine in ethyl acetate to yield adenosine analogue 61 (1.0 g, 85% yield) as a light tan solid foam. $^1$H NMR (DMSO-d6): δ7.85 (s, 1H), 7.80 (s, 1H), 7.50-7.20 (m, 10H), 7.14-6.98 (m, 17H), 5.38-5.29 (m, 1H), 4.50-4.42 (m, 1H), 3.00 (dd, J=9.3, J=4.8, 1H), 2.76-2.70 (m, 1H), 2.32-2.22 (m, 1H), 2.05-1.84 (m, 3H), 1.67-1.55 (m, 1H), 0.92 (s, 9H).

Example 58

N-(9-((1S,2R,3S)-3-((tert-Butyldiphenylsilyl)oxy)-2-((trityloxy)methyl)cyclopentyl)-9H-purin-6-yl)benzamide (62)

Benzoyl chloride (0.28 g, 0.231 ml, 2.0 mmol) was added dropwise to a cooled (ice-water bath) solution of compound 61 (0.97 g, 1.33 mmol) in anhydrous pyridine (10 ml). The bath was removed and reaction was stirred overnight, then cooled (ice-water bath) and treated with 2.5 ml of 7 N NH$_3$/

MeOH (added over 5 min). The reaction was removed from the bath, stirred under argon for 3 h to decompose the bis-benzoylated by-product and then concentrated in vacuo. The resultant residue was diluted with EtOAc and washed with 10% citric acid, saturated NaHCO$_3$, saturated NaCl, dried over MgSO$_4$ and concentrated in vacuo. The obtained material was chromatographed on silica eluting with 1:1 ethyl acetate: dichloromethane to give N-benzamide 62 (0.98 g, 88% yield) as a white sold foam.

$^1$H NMR (DMSO-d6): δ11.06 (s, 1H), 8.30 (s, 1H), 8.19 (s, 1H), 8.05-8.01 (m, 2H), 7.65-7.20 (m, 13H), 7.17-7.10 (m, 9H), 7.02-6.95 (m, 6H), 5.55-5.45 (m, 1H), 4.52-4.45 (m, 1H), 3.05 (dd, J=9.6, J=4.5, 1H), 2.85-2.78 (m, 1H), 2.40-2.30 (m, 1H), 2.05-1.92 (m, 2H), 1.89-1.67 (m, 2H), 0.94 (s, 9H).

Example 59

N-(9-((1S,2R,3S)-3-Hydroxy-2-(hydroxymethyl)cyclopentyl)-9H-purin-6-yl)benzamide (63)

A solution of 62 (0.95 g, 1.139 mmol) in a mixture of TFA (15 ml) and water (5 ml) was stirred under argon for 10 min. then concentrated and co-evaporated twice with water to remove residual TFA. The obtained residue was purified by column chromatography (silica gel, gradient 10-20% MeOH in dichloromethane) to afford N-benzoyl adenosine analogue 63 (0.36 g, 89% yield) as a white solid.

$^1$H NMR (DMSO-d6): δ11.10 (s, 1H), 8.71 (s, 1H), 8.46 (s, 1H), 8.06-8.02 (m, 2H), 7.67-7.52 (m, 3H), 5.27 (q, J=8.1 Hz, 1H), 4.88 (d, J=4.8 Hz, 1H), 4.32 (t, J=4.6, 1H), 4.28-4.20 (m, 1H), 3.29-3.23 (m, 1H), 2.95-2.90 (m, 1H), 2.36-2.20 (m, 4H), 1.63-1.55 (m, 1H).

Example 60

N-(9-((1S,2R,3S)-2-((Bis(4-methoxyphenyl)(phenyl)methoxy)methyl)-3-hydroxycyclopentyl)-9H-purin-6-yl)benzamide (64)

A solution of 63 (0.33 g, 0.93 mmol) in anhydrous pyridine (5 ml) and dimethoxytrityl chloride (0.348 g, 1.03 mmol) was kept at room temperature overnight, then concentrated and re-dissolved in ethyl acetate. The solution was washed twice with 10% citric acid, once with sodium bicarbonate, brine, dried over MgSO$_4$, and concentrated. The resultant mixture was chromatographed on silica eluting with 3% MeOH in dichloromethane to afford desired DMT derivative 64 (0.27 g, 44% yield) as a white solid.

$^1$H NMR (DMSO-d6): δ11.11 (s, 1H), 8.52 (s, 1H), 8.29 (s, 1H), 8.06-8.03 (m, 2H), 7.67-7.61 (m, 1H), 7.58-7.52 (m, 2H), 7.21-7.08 (m, 5H), 6.94-6.86 (m, 4H), 6.75-6.68 (m, 4H), 5.49-5.43 (m, 1H), 4.94 (d, J=5.7 Hz, 1H), 4.25-4.17 (m, 1H), 3.69 (s, 3H), 3.68 (s, 3H), 3.06 (dd, J=9.3 Hz, J=4.2 Hz, 1H), 2.58-2.50 (m, 1H), 2.45-2.05 (m, 4H), 1.63-1.55 (m, 1H).

Example 61

(1S,2R,3S)-3-(6-Benzamido-9H-purin-9-yl)-2-bis((4-methoxyphenyl)(phenyl)methoxy)methyl)cyclopentyl(2-cyanoethyl)diisopropylphosphoramidite (65)

2-Cyanoethyl N,N,N',N'-tetraisopropylphosphordiamidite (0.179 g, 0.595 mmol) was added to mixture of compound 64 (0.27 g, 0.417 mmol) and diisopropylammonium tetrazolide (0.078 g, 0.457 mmol) in dry dichloromethane (5 ml) under argon. The reaction was stirred for 15 h and treated with another portion (55 mg) of 2-cyanoethyl N,N,N',N'-tetraisopropylphosphordiamidite to complete the phosphoramidite formation. Saturated sodium bicarbonate solution and ethyl acetate were added. The organic phase was separated, washed with brine, dried over Na$_2$SO$_4$, and concentrated. The obtained material was re-precipitated by dissolving in a small amount of ethyl acetate and adding excess hexane followed by decanting the liquid phase. Drying in vacuo afforded phosphoramidite 65 (0.32 g, 82% yield) as a white solid foam.

$^{31}$P NMR CDCl$_3$): δ147.80, 147.57.

REFERENCES CITED

The following documents and publications are hereby incorporated by reference.

U.S. and Foreign Patent Documents

U.S. Pat. No. 7,153,955
U.S. Pat. No. 6,506,896
U.S. Pat. No. 7,045,610
U.S. Pat. No. 5,824,796
U.S. Pat. No. 6,127,121
U.S. Pat. No. 5,912,340
U.S. Patent Application Publication No. 2012/0015358
U.S. Patent Application Publication No. 2012/0244535
PCT Publication WO 01/38584
PCT Publication WO 01/64958

Non-Patent References

Nielsen et al, Science 254: 1497-1500 (1991)
Koshkin et al, *Tetrahedron* 54: 3607-30 (1998)
Viaivan et al. Artificial DNA: PNA & XNA, 2: 50-59 (2011)
Ueno et al., Nucl. Acids Symposium Series., 51: 293-294 (2007)
Devi and Ganesh, Artificial DNA: PNA & XNA. 1; 2; 1-8 (2010)
Johnson et al., J. Ora. Chem., 76:7964-74 (2011)
Zhang et al., J. Amer. Chem. Soc., 127: 4174-4175 (2005)
Asanuma et al., J Am Chem Soc., 132:14702-14703 (2010)
Peterson al., Organic & Biomolecular Chemistry, 1, 3293-3296 (2003)
Guillarme et al., Tetrahedron, 59: 2177-2184(2003)
Froehler and Matteucci, Nucl. Acids Res., 11: 8031-8036 (1983)
McBride et al., J. Amer. Chem. Soc., 108: 2040 (1986)
Tanaka et al., Nucl. Acids. Res., 33: 903-911 (2005)
W. H. Ham et al. J. Org. Chem. 2000, 65, 8372-8374
Bolli et al., Nuclic Acids Res., 24:4660-4667 (1996)
Sambrook, Fritsch & Maniatis, MOLECULAR CLONING: A LABORATORY MANUAL, Second Edition, Cold Spring Harbor Laboratory Press (1989)
Ausubel, et al., CURRENT PROTOCOLS IN MOLECULAR BIOLOGY, John Wiley & Sons (1987, 1988, 1989, 1990, 1991, 1992, 1993, 1994, 1995, 1996)
Gait (ed.), OLIGONUCLEOTIDE SYNTHESIS: A PRACTICAL APPROACH, IRL Press (1984)
Eckstein (ed.), OLIGONUCLEOTIDES AND ANALOGUES: A PRACTICAL APPROACH, IRL Press (1991)

What is claimed is:

1. Nucleoside analogues of Formula I:

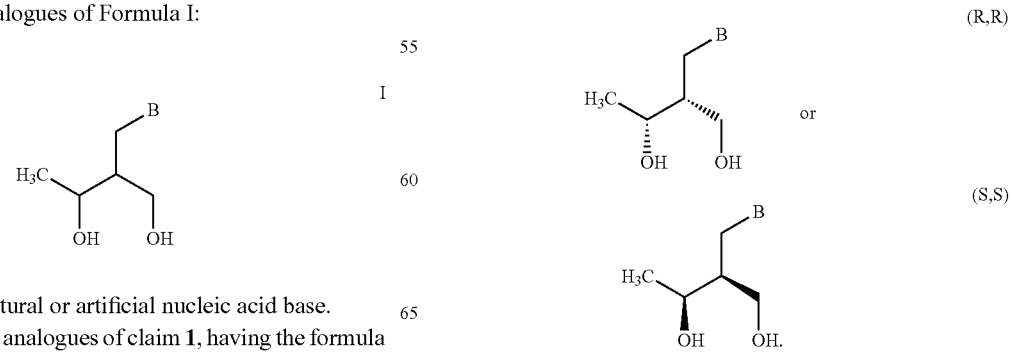

wherein B is a natural or artificial nucleic acid base.

2. The nucleoside analogues of claim 1, having the formula and stereochemistry:

3. An oligomer comprising one or more nucleoside analogues of claim 1.

4. The oligomer of claim 3 comprising one or more phosphodiester bonds.

5. An oligomer conjugate comprising an oligomer of claim 3 and an oligomer comprising natural nucleosides.

* * * * *

SEQUENCE LISTING

<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Oligonucleotide with variable A/T composition
      for melting curve analysis of homoduplex
<220> FEATURE:
<221> NAME/KEY: misc_feature
<222> LOCATION: (12)..(12)
<223> OTHER INFORMATION: n is T connected to hexanol linker

<400> SEQUENCE: 1
tacaagattt an                                                           12

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide with variable A/T composition
      for melting curve analysis of homoduplex
<220> FEATURE:
<221> NAME/KEY: misc_feature
<222> LOCATION: (12)..(12)
<223> OTHER INFORMATION: n is C connected to hexanol linker

<400> SEQUENCE: 2
tacaagattt an                                                           12

<210> SEQ ID NO 3
<211> LENGTH: 12
<212> TYPE: DNA
<213> ORGANISM: Artificial Sequence
<220> FEATURE:
<223> OTHER INFORMATION: Oligonucleotide with variable A/T composition
      for melting curve analysis of homoduplex
<220> FEATURE:
<221> NAME/KEY: misc_feature
<222> LOCATION: (12)..(12)
<223> OTHER INFORMATION: n is C connected to hexanol linker

<400> SEQUENCE: 3
ttcaagatgt an                                                           12

<210> SEQ ID NO 4
<211> LENGTH: 12
<212> TYPE: DNA
<213> ORGANISM: Artificial Sequence
<220> FEATURE:
<223> OTHER INFORMATION: Oligonucleotide with variable A/T composition
      for melting curve analysis of homoduplex
<220> FEATURE:
<221> NAME/KEY: misc_feature
<222> LOCATION: (12)..(12)
<223> OTHER INFORMATION: n is G connected to hexanol linker

<400> SEQUENCE: 4
tccaccgtcg an                                                           12

<210> SEQ ID NO 5
<211> LENGTH: 12
<212> TYPE: DNA
<213> ORGANISM: Artificial Sequence
<220> FEATURE:
<223> OTHER INFORMATION: Complement with variable A/T composition for
      melting curve analysis of homoduplex

```
<220> FEATURE:
<221> NAME/KEY: misc_feature
<222> LOCATION: (12)..(12)
<223> OTHER INFORMATION: n is A connected to hexanol linker

<400> SEQUENCE: 5
ataaatcttg tn                                                              12

<210> SEQ ID NO 6
<211> LENGTH: 12
<212> TYPE: DNA
<213> ORGANISM: Artificial Sequence
<220> FEATURE:
<223> OTHER INFORMATION: Complement with variable A/T composition for
      melting curve analysis of homoduplex
<220> FEATURE:
<221> NAME/KEY: misc_feature
<222> LOCATION: (12)..(12)
<223> OTHER INFORMATION: n is A connected to hexanol linker

<400> SEQUENCE: 6
gtaaatcttg tn                                                              12

<210> SEQ ID NO 7
<211> LENGTH: 12
<212> TYPE: DNA
<213> ORGANISM: Artificial Sequence
<220> FEATURE:
<223> OTHER INFORMATION: Complement with variable A/T composition for
      melting curve analysis of homoduplex
<220> FEATURE:
<221> NAME/KEY: misc_feature
<222> LOCATION: (12)..(12)
<223> OTHER INFORMATION: n is A connected to hexanol linker

<400> SEQUENCE: 7
gtacatcttg an                                                              12

<210> SEQ ID NO 8
<211> LENGTH: 12
<212> TYPE: DNA
<213> ORGANISM: Artificial Sequence
<220> FEATURE:
<223> OTHER INFORMATION: Complement with variable A/T composition for
      melting curve analysis of homoduplex
<220> FEATURE:
<221> NAME/KEY: misc_feature
<222> LOCATION: (12)..(12)
<223> OTHER INFORMATION: n is A connected to hexanol linker

<400> SEQUENCE: 8
ctcgacggtg gn                                                              12
```